(12) United States Patent
Jozefiak et al.

(10) Patent No.: US 11,491,183 B2
(45) Date of Patent: *Nov. 8, 2022

(54) SUBSTITUTED PHENYL BORONIC ACID CONTAINING POLYMERS AND METHODS OF USE

(71) Applicant: Glyscend, Inc., Baltimore, MD (US)

(72) Inventors: Thomas Henry Jozefiak, Belmont, MA (US); Ashish Nimgaonkar, Ellicott City, MD (US); Steven C. Polomoscanik, Belmont, MA (US)

(73) Assignee: Glyscend, Inc., Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/715,625

(22) Filed: Apr. 7, 2022

(65) Prior Publication Data

US 2022/0265703 A1    Aug. 25, 2022

Related U.S. Application Data

(60) Division of application No. 17/539,598, filed on Dec. 1, 2021, which is a continuation of application No. PCT/US2020/051506, filed on Sep. 18, 2020.

(60) Provisional application No. 62/903,328, filed on Sep. 20, 2019.

(51) Int. Cl.
| | | |
|---|---|---|
| *A61K 45/06* | (2006.01) | |
| *C08F 271/00* | (2006.01) | |
| *A61K 31/785* | (2006.01) | |
| *A61P 3/10* | (2006.01) | |
| *A61K 31/80* | (2006.01) | |

(52) U.S. Cl.
CPC ............ *A61K 31/785* (2013.01); *A61K 31/80* (2013.01); *A61K 45/06* (2013.01); *A61P 3/10* (2018.01); *C08F 271/00* (2013.01)

(58) Field of Classification Search
None
See application file for complete search history.

(56) References Cited

U.S. PATENT DOCUMENTS

| 6,287,285 | B1 | 9/2001 | Michal et al. |
|---|---|---|---|
| 7,943,713 | B2 | 5/2011 | Pelton et al. |
| 7,998,412 | B2 | 8/2011 | Burles et al. |
| 8,048,680 | B2 | 11/2011 | Lowe et al. |
| 8,241,574 | B2 | 8/2012 | Burles et al. |
| 8,668,871 | B2 | 3/2014 | Matsumoto et al. |
| 9,114,177 | B2 | 8/2015 | Kataoka et al. |
| 10,973,846 | B2 | 4/2021 | Karp et al. |
| 11,090,354 | B2 | 8/2021 | Jozefiak et al. |
| 2003/0059399 | A1 | 3/2003 | Holmes-Farley et al. |
| 2006/0134062 | A1 | 6/2006 | Huval et al. |
| 2008/0057086 | A1 | 3/2008 | Etter et al. |
| 2011/0059176 | A1 | 3/2011 | Moro et al. |
| 2012/0283403 | A1 | 11/2012 | Matsumoto et al. |
| 2013/0066264 | A1 | 3/2013 | Matsumoto et al. |
| 2014/0080937 | A1 | 3/2014 | Yukawa |
| 2014/0288398 | A1 | 9/2014 | Simberg et al. |
| 2016/0354509 | A1 | 12/2016 | Parlato et al. |
| 2018/0228863 | A1 | 8/2018 | Jozefiak et al. |
| 2018/0236127 | A1 | 8/2018 | Parlato et al. |
| 2018/0327972 | A1 | 11/2018 | Zhang et al. |
| 2022/0088062 | A1 | 3/2022 | Jozefiak et al. |
| 2022/0088063 | A1 | 3/2022 | Jozefiak et al. |
| 2022/0226366 | A1 | 7/2022 | Jozefiak et al. |

FOREIGN PATENT DOCUMENTS

| CN | 103865060 | | 6/2014 |
|---|---|---|---|
| EP | 2522679 | A1 | 11/2012 |
| EP | 2578234 | B1 | 7/2017 |
| JP | 2007177014 | A | 7/2007 |
| WO | 2004009136 | A2 | 1/2004 |
| WO | 2004/081624 | A1 | 9/2004 |
| WO | 2008/144615 | A1 | 11/2008 |
| WO | 2010/044930 | A2 | 4/2010 |
| WO | 2014/151565 | A1 | 9/2014 |
| WO | 2015/120471 | A1 | 8/2015 |
| WO | 2017/024237 | A1 | 2/2017 |
| WO | 2017/061435 | A1 | 4/2017 |
| WO | 2017/070617 | A1 | 4/2017 |
| WO | 2020/061430 | A1 | 3/2020 |
| WO | 2021/055752 | A1 | 3/2021 |
| WO | 2021/055759 | A1 | 3/2021 |

OTHER PUBLICATIONS

Zhao et al. "Boronic Acid as Glucose-Sensitive Agent Regulates Drug Delivery for Diabetes Treatment" Materials (2017) 10, 170; pp. 1-14.
Metabolic Disorders (2022), NIH, Genetic and Rare Diseases Information Center, obtained from https://rarediseases.info.nih.gov/diseases/diseases-by-category/14/metabolic-disorders (accessed Jun. 3, 2022, 2:20 PM).
Berkrot, B. "Novo Nordisk diabetes drug fails to help heart failure: study" (2015), Reuters, obtained from https://www.reuters.com/article/US-health-heart-novonordisk/novo-nordisk-diabetes-drug-fails-to-help-heart-failure-study-idUSKCN0SX0X620151108.
Cambre, et al, "Biomedical applications of boronic acid polymers", Polymer (2011), vol. 52, No. 21, pp. 4631-4643.
Li, et al, "Synthesis and Development of Poly(N-Hydroxyethyl Acrylamide)-Ran-3-Acrylamidophenylboronic Acid Polymer Fluid for Potential Application in Affinity Sensing of Glucose", Journal of Diabetes Science and Technology (2011), vol. 5, No. 5, pp. 1060-1067.
Palavan-Unsal, et al, "Polyamines in tea processing", International Journal of Food Sciences and Nutrition, (2007), vol. 58, No. 4, pp. 304-311.
Goetheer, et al, "Functionalized Poly(propylene imine) Dendrimers as Novel Phase Transfer Catalysts in Supercritical Carbon Dioxide," Ind. Eng. Chem. Res. (2000), vol. 39, No. 2, pp. 4634-4640.

(Continued)

*Primary Examiner* — Celeste A Roney
(74) *Attorney, Agent, or Firm* — Hogan Lovells US LLP

(57) ABSTRACT

The disclosure relates to cationic polymers functionalized with substituted phenylboronic acid groups and to methods of using the same to treat metabolic and gastrointestinal disorders.

19 Claims, 3 Drawing Sheets

(56) References Cited

OTHER PUBLICATIONS

Seno et al., "pH- and sugar-sensitive multilayer films composed of phenylboronic acid (PBA)-modified poly(allylamine hydrochloride) (PBA-PAH) and poly(vinyl alcohol) (PVA): A significant effect of PBA content on the film stability," Materials Science and Engineering C (2016), 62, 474-479.

Sato et al., "H2O2-Induced Decomposition of Layer-by-Layer Films Consisting of Phenylboronic Acid-Bearing Poly (allylamine) and Poly(vinyl alcohol)," Langmuir (2014), 30, 9247-9250.

Fuhrmann, "Luminal coating of the intestine," Nature Materials (2018), 17, 754-755.

Lee et al., "Therapeutic luminal coating of the intestine," Nature Materials (2018), 17, 834-842.

Jozefiak, T. H. et al. "Benzoxaborole Polymers and Methods of Use," unpublished U.S. Appl. No. 17/642,807.

Patani, G. A. et al., "Bioisosterism: A Rational Approach in Drug Design," Chem. Rev. (1996) 96:3147-3176.

Final Office Action issued in U.S. Appl. No. 17/539,611, dated Aug. 12, 2022.

Brooks et al. "Synthesis and Applications of Boronic Acid-Containing Polymers: From Materials to Medicine" Chemical Reviews (2016) 116, 1375-1397.

Kabilan et al. "Holographic glucose sensors", Biosensors and Bioelectronics 20 (2005), 1602-1610.

Kataoka et al. "Totally Synthetic Polymer Gels Responding to External Glucose Concentration: Their Preparation and Application to On-Off Regulation of Insulin Release" J. Am. Chem. Soc. (1998), 120, 12694-12695.

Kitano et al. "Glucose-responsive complex formation between poly(vinyl alcohol) and poly(N-vinyl-2-pyrrolidone) with pendent phenylboronic acid moieties" Makromol. Chem., Rapid Commun. (1991) 12:227-233.

Koliaki, C. et al., "The role of bariatric surgery to treat diabetes: current challenges and perspectives," BMC Endocr Disord. (2017) 17:50.

Kotsuchibashi, Y. et al. "Temperature, pH, and glucose responsive gels via simple mixing of boroxole- and glyco-based polymers," ACS Macro Letters (2013) 2:260-264.

Kudo, Y. et al. "Controlled water-soluble properties of poly(vinyl alcohol) films via the benzoxaborole-containing temperature-responsive copolymers" Polymer, (2019), 175:1-7.

Lan et al., "Phenylboronic acid-decorated polymeric nanomaterials for advanced bio-application" Nanotechnol Rev (2019)8:548-561.

Matsumoto et al. "Glucose-responsive polymer gel bearing phenylboroate derivative as a glucose-sensing moiety operating at the physiological pH" Biomacromolecules (2004) 5:1038-1045.

Ravaine et al. "Chemically controlled closed-loop insulin delivery" Journal of Controlled Release (2008) 132: 2-11.

Zenkl et al. "Fluorescent acrylamide nanoparticles for boronic acid based sugar sensing—from probes to sensors" Microchim. Acta (2009) 166:123-131.

International Search Report and Written Opinion for PCT/US2019/052110, dated Jan. 13, 2020.

International Search Report and Written Opinion for PCT/US2020/051506, dated Dec. 18, 2020.

International Search Report for PCT/US2020/051499, dated Aug. 2, 2021.

Written Opinion of the International Searching Authority for PCT/US2020/051499.

Murabayashi et al. "In vitro evaluation of newly developed adsorbent for selective removal of glycosylated low-density lipoprotein," Therapeutics Apheresis (2002) 6(6):425-430.

Wu et al. "Multifunctional Hybrid Nanogel for Integration of Optical Glucose Sensing and Self-Regulated Insulin Release at Physiological pH" ACS Nano (2010) 4(8):4831-4839.

SUBSTITUTED PHENYL BORONIC ACID CONTAINING POLYMERS AND METHODS OF USE

RELATED APPLICATIONS

This application filed under 35 U.S.C. 111(a) is a divisional of U.S. application Ser. No. 17/539,598, filed on Dec. 1, 2021, which is a continuation of International Application No. PCT/US2020/051506, filed on Sep. 18, 2020, which claims the benefit of U.S. Provisional Application No. 62/903,328, filed on Sep. 20, 2019. The entire teachings of the above applications are incorporated herein by reference.

BACKGROUND OF THE INVENTION

Type-2 diabetes mellitus (T2DM) affects about 11.3% of the U.S. adult population, with 35% of the U.S. adults having pre-diabetic symptoms. U.S. healthcare costs due to diabetes are approaching $200 billion annually. The incidence of T2DM continues to increase in parallel with the obesity epidemic, and a major portion of present treatment for T2DM consists of a regimen of oral medications that may be suboptimal for many subjects, in part because of side effects associated with systemic absorption of their medication. Bariatric surgery to bypass or exclude the duodenum from the digestive tract has been shown to improve T2DM. The Diabetes Surgery Summit recommends bariatric surgery to treat T2DM in some obese patients (grade III obesity), and that bariatric surgery should be considered for treatment of other patients. (See, e.g., Koliaki, C. et al., BMC Endocr Disord. (2017) 17:50 DOI 10.1186/s12902-017-0202-6.)

Analysis of the typical diabetic patient's path from first line drugs to insulin and on to surgery and other highly invasive treatments reveals striking gaps, not limited to ineffective treatments and clinical inertia. Surgery and other solutions also have failed to achieve widespread adoption. The addition of specialist clinicians in the care pathway has contributed to those failures. Accordingly, an effective treatment in the hands of the primary care physician would likely reach a much larger segment of the subject population than those which require a specialist, such as an endocrinologist, a gastroenterologist, or a surgeon, and would therefore have much greater impact.

US 2006/0134062 disclose polymers in which certain arylboronic acid moieties are bonded to the polymer backbone through long linkers, and the use of such polymers as inhibitors of lipase. The polymer backbone is said to be not critical for lipase inhibition.

U.S. Pat. No. 7,943,713 disclose certain polyamine boronic acid derivatives and their use to increase paper wet web strength and wet strength. The preferred polymers are characterized by aryl boronic acid moieties that are directly bonded to a carbon atom in the polymer backbone, or bonded to a carbon atom in the polymer backbone through an amide linkage.

WO 2017/024237 discloses certain cationic polymers and use of the polymers for complexing mucus to form an occlusive barrier in the duodenum.

Seno, M. et. al, Materials Science and Engineering C, 62 (2016) 474-479, discloses certain pH- and sugar-sensitive multilayer films that are composed of phenylboronic acid-modified poly(allylamine hydrochloride) and pol(vinyl alcohol). Sato, K. et al, Langmuir, 2014, 30, 9247-9250, also discloses multilayer films that are composed of phenylboronic acid-modified poly(allylamine hydrochloride) and pol (vinyl alcohol).

A need therefore exists for new medications and non-invasive methods for treating subjects with T2MD and related metabolic disorders.

SUMMARY OF THE INVENTION

The invention provides polymer compositions for forming a physical barrier in the gastrointestinal (GI) tract of a subject between the intestinal lining and the luminal contents. The polymers of the invention are mucin-interacting agents which form a physical barrier in-situ by interaction with resident mucin in the GI tract.

The inventors have discovered that the incorporation of pendant substituted phenyl boronic acid moieties into certain cationic polymers dramatically improved the mucin-complexing activity of the polymers.

As shown in the examples, the polymers described herein have improved mucin and mucus complexing activity in comparison to comparable cationic polymers, and can effectively condense mucin and mucus at the pH of the duodenum. The polymers bind tightly to mucus at the pH of the duodenum and once bound to mucus are resistant to removal by high concentrations of salts (e.g., 1M NaCl). The resulting polymer-mucus complexes have dramatically different properties in comparison to free mucus.

This disclosure relates to cationic polymers that contain pendant substituted phenyl boronic acid groups, which are bonded directly or indirectly to the polymer backbone through an amine or amide bond, and to a method of treating metabolic diseases that include administering a therapeutically effective amount of such a polymer to a subject in need thereof.

Another aspect of the invention is a pharmaceutical composition comprising the polymers of the present invention, along with a carrier or diluent. The pharmaceutical composition can be used for therapy, such as in the treatment of a disorder described herein. Similarly, the invention provides for the use of a polymer disclosed herein as a medicament and for the use of a polymer disclosed herein in the manufacture of a medicament for the treatment of a disorder described herein.

BRIEF DESCRIPTION OF THE DRAWINGS

FIG. 2 depicts the blood glucose levels over a course of 120 minutes from each group following glucose administration.

DETAILED DESCRIPTION OF THE INVENTION

Figure 1:
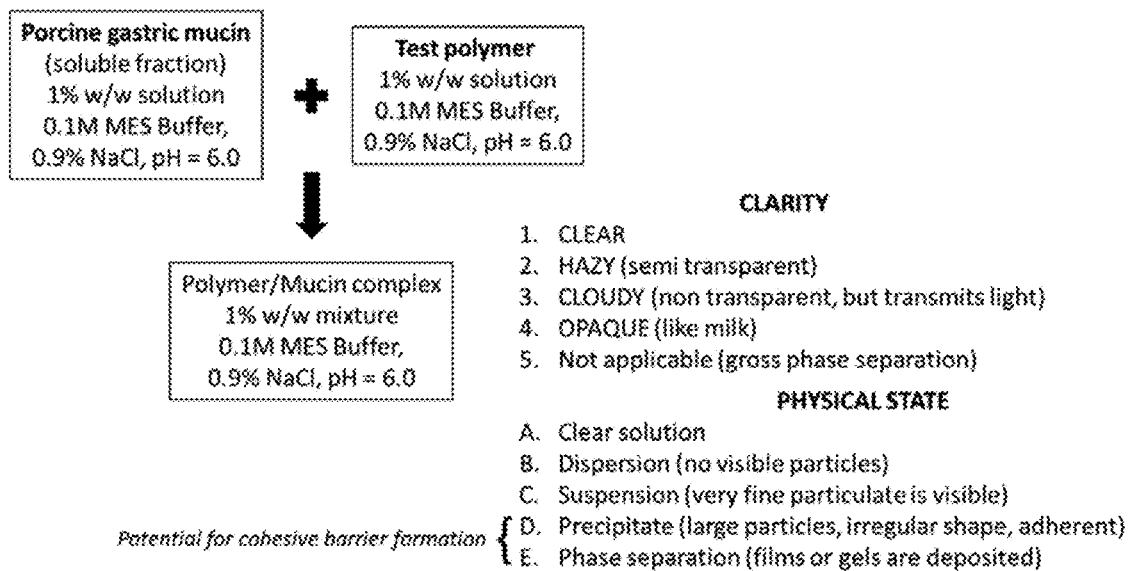
FIG. 1 illustrates the mucin complexing assay.

This disclosure relates to cationic polymers that contain pendant substituted phenyl boronic acid groups, which are bonded directly or indirectly to the polymer backbone through an amine or amide bond. The cationic polymers are preferably polycations that include amine- or ammonium containing repeat units, and if desired may contain other cationic groups such as imidazolyl, pyridinyl, and guanidino. The substituted phenyl boronic acid polymers preferably contain both cationic repeat units and substituted phenyl boronic acid repeat units. The pendant phenyl boronic acid moiety is substituted with one or more suitable substituents, which include electron withdrawing groups, electron donating groups, as described herein. In some embodiments the polymers may contain a repeat unit that contains a cationic group and a substituted phenyl boronic acid group. The cationic polymers can be co-polymers that also contain any desired neutral or anionic repeat units, as further described herein, provided that the polymer retains a net cationic charge.

Pharmaceutical compositions comprising these polymers and methods of treatment using these polymers to treat metabolic disorders, such as Type-2 diabetes mellitus (T2DM), Type-1 diabetes mellitus (T1DM), prediabetes, hyperlipidemia, obesity, overweight, metabolic syndrome, non-alcoholic steatohepatitis, non-alcoholic fatty liver, and polycystic ovary syndrome (PCOS) are also disclosed.

Exemplary polymers comprise a substituted phenyl boronic acid moiety-containing repeat unit of Formula (I)-(III).

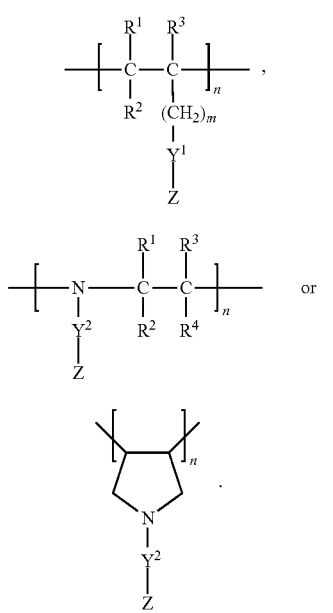

In Formulas (I) through (III):
$R^1$, $R^2$, $R^3$ and $R^4$ are independently hydrogen or substituted or unsubstituted alkyl;
$Y^1$ in each occurrence is independently a direct bond or -$L^1$-$A^1$-$L^2$-$A^2$-;
$L^1$ in each occurrence is —$NR^9$—, —NC(O)— or —C(O)N—;
$L^2$ in each occurrence is absent, —$NR^9$—, —O— or —S—;
$Y^2$ in each occurrence is independently a direct bond or -$L^3$-$A^1$-$L^2$-$A^2$-;
$L^3$ in each occurrence is —C(O)— or absent;
$L^2$ in each occurrence is absent, —$NR^9$—, —O— or —S—;
$A^1$ and $A^2$ in each occurrence are independently absent or optionally substituted $C_1$-$C_5$ alkylene;
$R^9$, $R^{10}$ and $R^{11}$ in each occurrence are independently hydrogen or substituted or unsubstituted alkyl (preferably a substituted or unsubstituted $C_1$-$C_6$ alkyl);

Z in each occurrence is

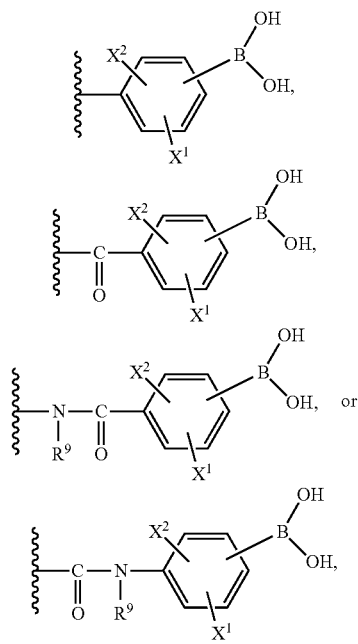

preferably the —B(OH)$_2$ is at the 3- or 4-position of the phenyl ring;
$X^1$ and $X^2$ are independently selected from a group consisting of hydrogen, halo, —CN, —NO$_2$, —N+($R^9$)($R^{10}$)($R^{11}$), —CF$_3$, —SO$_3$($R^9$), —SO$_2$($R^9$), —CON($R^9$)($R^{10}$), —(CH$_2$)$_m$—N($R^9$)($R^{10}$), and —O$R^9$;
n is an integer from 1 to 100,000 and
m is an integer from 0 to 4;
with the proviso that no more than one of $X^1$ and $X^2$ is hydrogen;
when either $X^1$ or $X^2$ is —(CH$_2$)$_m$—N($R^9$)($R^{10}$), it is bonded to the carbon atom in the phenyl ring that is adjacent to the carbon atom in the phenyl ring to which —B(OH)$_2$ is bonded, and the other of $X^1$ and $X^2$ is hydrogen.

In some embodiments of Formulas (I)-(III), $X^1$ is halo, —CN, —NO$_2$, —N$^+$($R^9$)($R^{10}$)($R^{11}$), —CF$_3$, —SO$_3$($R^9$), —SO$_2$($R^9$), or —CON($R^9$)($R^{10}$), and $X^2$ is not —(CH$_2$)$_m$—N($R^9$)($R^{10}$) or —O$R^9$; or $X^1$ is —(CH$_2$)$_m$—N($R^9$)($R^{10}$) or —O$R^9$, and $X^2$ is not halo, —CN, —NO$_2$, —N+($R^9$)($R^{10}$)($R^{11}$)—CF$_3$, —SO$_3$H, or —CON($R^9$)($R^{10}$).

In some preferred aspects, the polymer contains a repeat unit of Formula (I).

Preferred repeat units of Formula (I) include repeat units of Formulas (Ia)-(If):

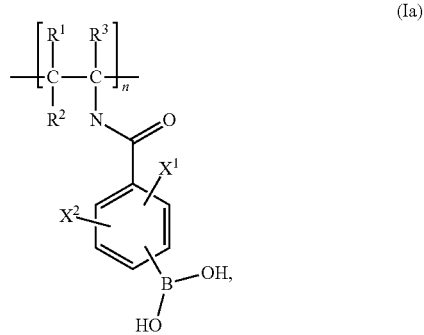

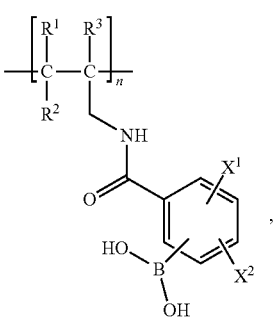
(Ib)

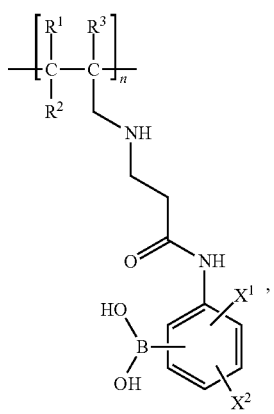
(Ic)

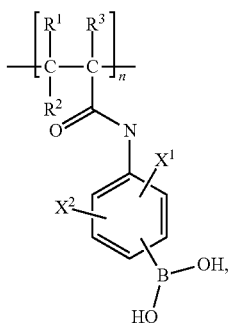
(Id)

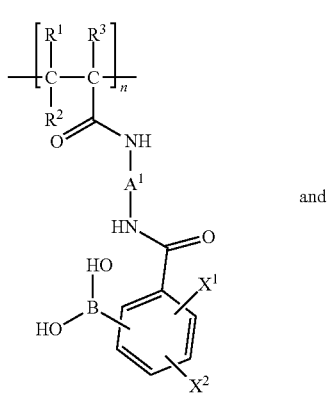
(Ie)

and

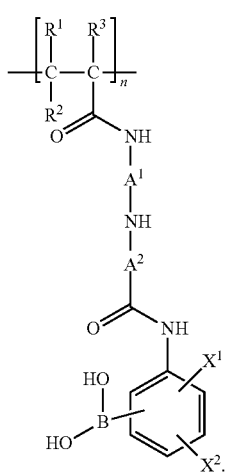
(If)

In Formulas (Ia) through (If), $R^1$, $R^2$, $R^3$, $A^1$, $A^2$, $X^1$, $X^2$, m and n are as described in Formula (I). In some embodiments, the —B(OH)$_2$ is at the 3-position of the phenyl ring. In other embodiments, the —B(OH)$_2$ is at the 4-position of the phenyl ring.

In some particular examples, the polymer includes a repeat unit of Formula (Ia), (Ib), (Ic), (Id), (Ie) or (If), wherein $R^1$, $R^2$ and $R^3$ are each hydrogen.

In other particular examples, the polymer includes a repeat unit of Formula (Ia), (Ib), (Ic), (Id), (Ie) or (If) wherein $R^1$ and $R^2$ are each hydrogen, and $R^3$ is alkyl, and preferably $R^3$ is methyl.

It is advantageous to have substituents such as halo, preferably fluoro, —CN, —NO$_2$, —N$^+$(R$^9$)(R$^{10}$)(R$^{11}$), —CF$_3$, —SO$_3$(R$^9$), —SO$_2$(R$^9$), and —CON(R$^9$)(R$^{10}$) on the phenyl boronic acid ring as these groups are electron withdrawing by nature and can lower the pKa of the boronic acid.

It is also advantageous to have substituents such as —(CH$_2$)$_m$—N(R$^9$)(R$^{10}$), preferably —(CH$_2$)—N(Me)$_2$, on the phenyl boronic acid ring adjacent to the boronic acid group, as this group is electron donating by nature and lowers the pKa value due to the interaction between B and N atoms.

Without wishing to be bound by any particular theory, it is believed that certain substituted phenyl boronic acid polymers have a lower pKa that unsubstituted phenyl boronic polymers which lead to greater sensitivity to the pH increase between the stomach and duodenum, enhancing the mucin-complexing activity of the polymers at the desired site of barrier formation.

In Formulas (I) through (III), $R^1$, $R^2$, $R^3$, $R^4$, $Y^1$, $Y^2$, m, n and Z are as described above, preferably the —B(OH)$_2$ is at the 3- or 4-position of the ring and $X^1$ and $X^2$ are at other positions of the ring.

In Formulas (I) through (III), $R^1$, $R^2$, $R^3$, $R^4$, $Y^1$, $Y^2$, m, n and Z are as described above, preferably the —B(OH)$_2$ is at the 3-position of the ring and $X^1$ and $X^2$ are at other positions of the ring.

In Formulas (I) through (III), $R^1$, $R^2$, $R^3$, $R^4$, $Y^1$, $Y^2$, m, n and Z are as described above, preferably the —B(OH)$_2$ is at the 4-position of the ring and $X^1$ and $X^2$ are at other positions of the ring.

In Formulas (I) through (III), $R^1$, $R^2$, $R^3$, $R^4$, $Y^1$, $Y^2$, m, n and Z are as described above, preferably the —B(OH)$_2$ is at the 3- or 4-position of the ring and either $X^1$ or $X^2$ is —(CH$_2$)$_m$—N(R$^9$)(R$^{10}$), and $X^2$ is bonded to the carbon atom in the phenyl ring that is adjacent to the carbon atom in the phenyl ring to which —B(OH)$_2$ is bonded, and the other of $X^1$ and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 3-position of the ring and either $X^1$ or $X^2$ is —(CH$_2$)$_m$—N(R$^9$)(R$^{10}$), and $X^2$ is bonded to the carbon atom in the phenyl ring that is adjacent to the carbon atom in the phenyl ring to which —B(OH)$_2$ is bonded, and the other of $X^1$ and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 4-position of the ring and either $X^1$ or $X^2$ is —(CH$_2$)$_m$—N(R$^9$)(R$^{10}$) that is bonded to the carbon atom in the phenyl ring that is adjacent to the carbon atom in the phenyl ring to which —B(OH)$_2$ is bonded, and the other of $X^1$ and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 3-position of the ring, $X^1$ is at the 5-position of the ring and is halo, preferably fluoro, and $X^2$ is hydrogen, halo, —CN, —NO$_2$, —N$^+$(R$^9$)(R$^{10}$)(R$^{11}$), —CF$_3$, —SO$_3$(R$^9$), —SO$_2$(R$^9$), or —CON(R$^9$)(R$^{10}$) at the 2-, 5- or 6-position of the ring.

In Formulas (I) through (III), $R^1$, $R^2$, $R^3$, $R^4$, $Y^1$, $Y^2$, m, n and Z are as described above, preferably the —B(OH)$_2$ is at the 4-position of the ring, $X^1$ is at the 2-position of the ring and is halo, preferably fluoro, and $X^2$ is hydrogen, halo, —CN, —NO$_2$, —N$^+$(R$^9$)(R$^{10}$)(R$^{11}$), —CF$_3$, —SO$_3$(R$^9$), —SO$_2$(R$^9$), or —CON(R$^9$)(R$^{10}$) at the 3-, 5- or 6-position of the ring.

In Formulas (I) through (III), $R^1$, $R^2$, $R^3$, $R^4$, $Y^1$, $Y^2$, m, n and Z are as described above, preferably the —B(OH)$_2$ is at the 3-position of the ring, $X^1$ is at the 5-position of the ring and is halo, preferably fluoro, and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 4-position of the ring, $X^1$ is at the 2-position of the ring and is halo, preferably fluoro, and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 4-position of the ring, $X^1$ is at the 2-position of the ring and is halo, preferably fluoro, and $X^2$ is halo, preferably fluoro at 3-, 5- or 6-position of the ring.

In Formulas (I) through (III), $R^1$, $R^2$, $R^3$, $R^4$, $Y^1$, $Y^2$, m, n and Z are as described above, preferably the —B(OH)$_2$ is at the 4-position of the ring, $X^1$ is at the 2-position of the ring and is halo, preferably fluoro, and $X^2$ is halo, preferably fluoro at 3-position of the ring.

In Formulas (I) through (III), $R^1$, $R^2$, $R^3$, $R^4$, $Y^1$, $Y^2$, m, n and Z are as described above, preferably the —B(OH)$_2$ is at the 4-position of the ring, $X^1$ is at the 2-position of the ring and is —CF$_3$ and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 3-position of the ring, either $X^1$ or $X^2$ is —(CH$_2$)$_m$—N(R$^9$)(R$^{10}$) that is bonded to the carbon atom in the phenyl ring that is adjacent to the carbon atom in the phenyl ring to which —B(OH)$_2$ is bonded, and the other of $X^1$ and $X^2$ is hydrogen.

In Formulas (I) through (III), $R^1$, $R^2$, $R^3$, $R^4$, $Y^1$, $Y^2$, m, n and Z are as described above, preferably the —B(OH)$_2$ is at the 4-position of the ring, either $X^1$ or $X^2$ is —(CH$_2$)$_m$—N(R$^9$)(R$^{10}$) that is bonded to the carbon atom in the phenyl ring that is adjacent to the carbon atom in the phenyl ring to which —B(OH)$_2$ is bonded, and the other of $X^1$ and $X^2$ is hydrogen.

In Formulas (Ia) through (If), $R^1$, $R^2$, $R^3$, $A^1$, $A^2$, m and n are as described in Formula (I), preferably —B(OH)$_2$ is at 4-position of the ring, $X^1$ is at the 2-position of the ring and is halo, preferably fluoro, and $X^2$ is hydrogen.

In Formulas (Ia) through (If), $R^1$, $R^2$, $R^3$, $A^1$, $A^2$, m and n are as described in Formula (I), preferably —B(OH)$_2$ is at 4-position of the ring, $X^1$ is a halo, preferably fluoro at 2-position of the ring and $X^2$ is halo, preferably fluoro at 3-position of the ring.

In Formulas (Ia) through (If), $R^1$, $R^2$, $R^3$, $A^1$, $A^2$, m and n are as described in Formula (I), preferably —B(OH)$_2$ is at 4-position of the ring, $X^1$ is —CF$_3$ at 2-position of the ring and $X^2$ is hydrogen.

In Formulas (Ia) through (If), $R^1$, $R^2$, $R^3$, $A^1$, $A^2$, m and n are as described in Formula (I), preferably —B(OH)$_2$ is at 3-position of the ring, $X^1$ is —(CH$_2$)$_m$—N(R$^9$)(R$^{10}$), preferably —CH$_2$—N(Me)$_2$ at 4-position of the ring and $X^2$ is hydrogen.

In Formulas (Ia) through (If), $R^1$, $R^2$, $R^3$, $A^1$, $A^2$, m and n are as described in Formula (I), preferably —B(OH)$_2$ is at 4-position of the ring, $X^1$ is —(CH$_2$)$_m$—N(R$^9$)(R$^{10}$), preferably —CH$_2$—N(Me)$_2$ at 3-position of the ring and $X^2$ is hydrogen.

In other preferred aspects, the polymer contains a repeat unit of Formula (II). In some examples of polymers that contain a repeat unit of Formula (II), $Y^2$ is a direct bond and Z is

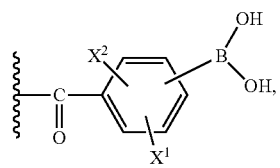

preferably the —B(OH)$_2$ is at the 3- or 4-position of the ring and $X^1$ and $X^2$ are as described above.

In other preferred aspects, the polymer contains a repeat unit of Formula (II). In some examples of polymers that contain a repeat unit of Formula (II), $Y^2$ is direct bond and Z is

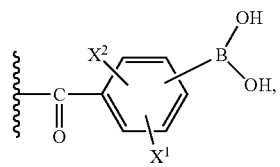

preferably the —B(OH)$_2$ is at the 3- or 4-position of the ring and $X^1$ and $X^2$ are as described above.

In other preferred aspects, the polymer contains a repeat unit of Formula (III). In some examples of polymers that contain a repeat unit of Formula (III), $Y^2$ is direct bond and Z is

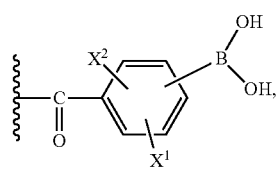

preferably the —B(OH)$_2$ is at the 3- or 4-position of the ring and X$^1$ and X$^2$ are as described above.

The polymers can be homopolymers. When homopolymers, the polymers contain a nitrogen-containing repeat unit (e.g. is a polyamine or polyamide) with pendant boronic acid moieties bonded to the polymer backbone directly or indirectly through the nitrogen atom of the repeat unit. Accordingly, the polymers typically contain secondary or tertiary amines, or quaternary ammonium if desired, to which the boronic acid moiety is bonded. The secondary or tertiary amines will be protonated at about pH 5-7, providing cationic polymers.

Preferably, the polymers are copolymers that contain a repeat unit of any one for Formulas (I)-(III) one or more other repeat units. The other repeat units are preferably cationic (e.g., a nitrogen-containing repeat unit), but can be neutral or anionic, provided that the polymer retains an overall cationic charge.

Preferred nitrogen-containing repeat units that can be modified to include pendant boronic acid moieties include poly(allylamine) (PAAn), poly(diallylamine) (PDAAn), poly(ethyleneimine) (PEI) and poly(methacrylamidopropylamine) (PMAPAn).

In the polymers disclosed herein, at least about 5% of the repeating chemical units contain a pendant boronic acid group, e.g., a repeat unit of any one of Formulas (I)-(III). In some instances, substantially all of the chemical repeat units in the polymer contain a pendant boronic acid group. Preferably, about 5% to about 50%, about 5% to about 40%, about 5% to about 30%, about 5% to about 20%, or about 5% to about 15% of the repeating chemical units contain a pendant boronic acid group.

Suitable nitrogen-containing repeat units for inclusion in the polymers are well-known in the art, and include for example, polyvinylamine, poly-N-alkylvinylamine, polyacrylamide, polyalkylacrylamides (e.g. polymethacrylamides), poly-N-alkylacrylamides, polyalkyl-N-alkylacrylamides, polyallylamine, poly-N-alkylallylamine, polydiallylamine, poly-N-alkyldiallylamine, polyethylenimine, polyaminostyrene, polyvinylimidazole, polyvinylpyridine, and the like.

Nitrogen-containing repeat units are cationic when the amino nitrogen is protonated. If desired the cationic character can be altered using known methods, such as, by converting amines into guanidino, biguanide, aromatics such as imidazolyl and pyridinyl, quaternary ammoniums, or by introducing additional amino groups e.g., by alkylating an amine with an alkylamino or alkylammonium group.

Polyamines typically are highly charged at duodenal pH (about pH 5-6), however, due to a high density of protonated amine sites in close proximity, they deprotonate to a small extent as they pass from the stomach (pH ~2) to the duodenum (pH ~5) following ingestion. Even a small amount of neutralization effectively lowers the polymer charge density and causes these polymer chains become more coiled, compact, and less well hydrated as pH is increased. Without wishing to be bound by theory, this pH responsiveness is believed to contribute to preferential complexing of the mucus in the duodenum over the stomach. Other polymers of this invention which are capable of responding to the pH increase of the duodenum contain cationic repeat units (e.g., repeat units with protonated amines) that have inductive or structural features resulting in a lower pKa value than that of a standard protonated aliphatic amine. The lower pKa of these protonated polymers results in a greater sensitivity to the pH increase coincident with transit from the stomach to the duodenum. These types of polymers can therefore be targeted to interact with the loose mucus of the proximal duodenum, and include polyamines substituted with polar groups, such as hydroxyl groups less than three carbon atoms away from the protonated amine. In some embodiments, the polymers include amines that are modified to have a lower pKa than the unmodified amines. For example, the cationic polymers can have pKa values less than 9.0, more preferably a pKa less than 8.0, and most preferably a pKa less than or equal to 7.0.

Suitable boronic acid containing repeat units for inclusion in the polymers described herein include, but not limited to, for example, repeat units of Formulas (I), (Ia)-(If), (II) and (III), including the following:

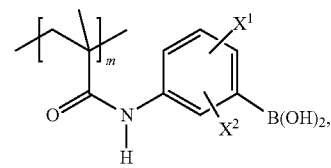

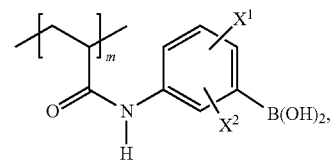

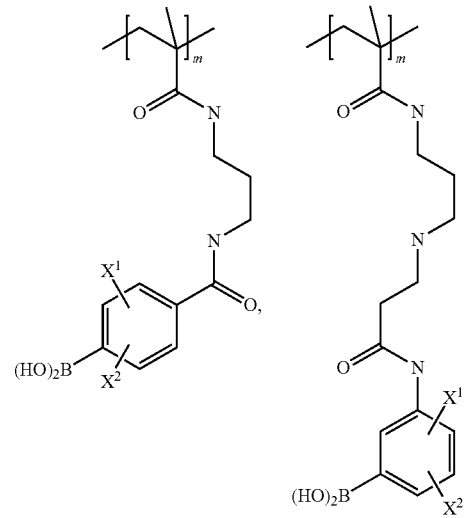

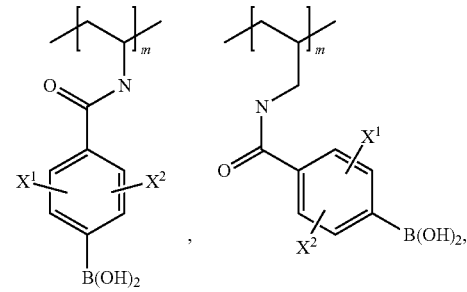

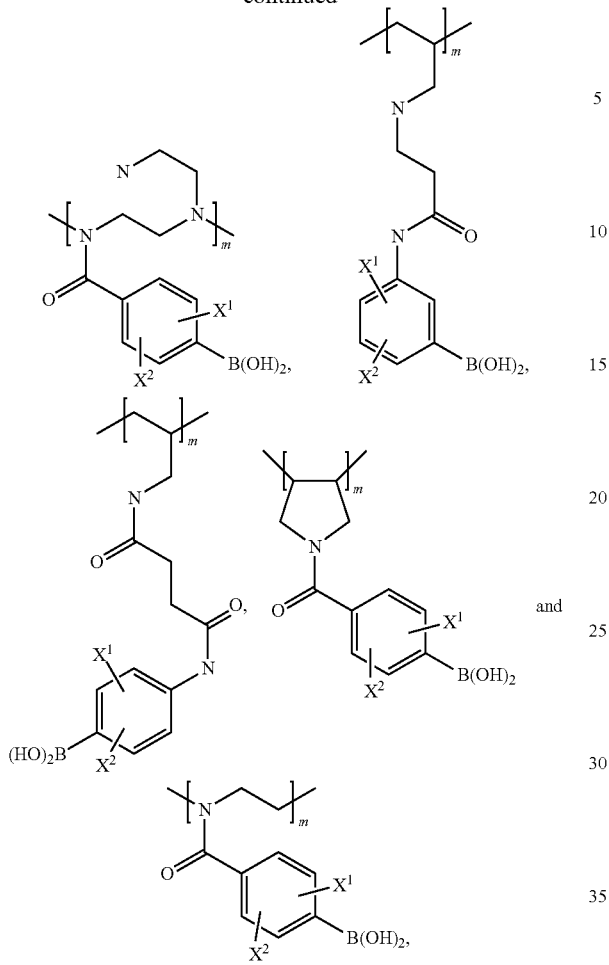
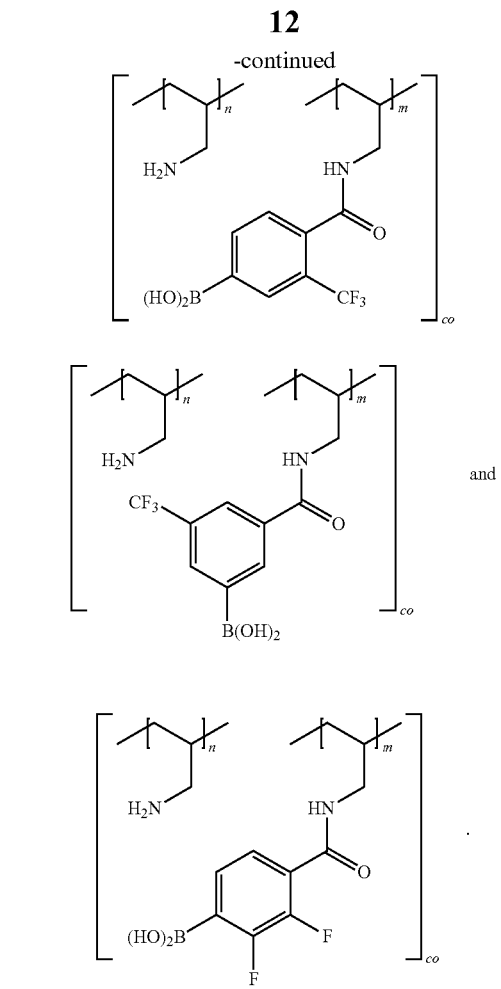
where "m" represents an integer from 1 to 100,000 and $X^1$ and $X^2$ are described as above.
Exemplary polymers that contain substituted phenyl boronic acid repeat units include the following:
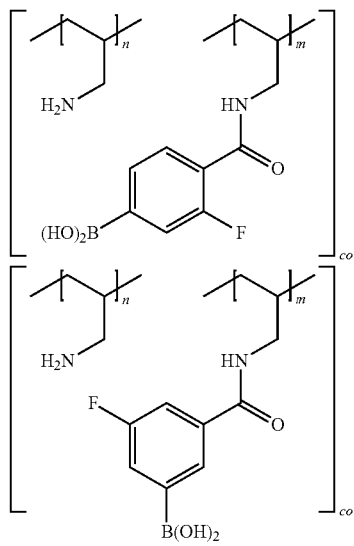
Exemplary polymers that contain substituted phenyl boronic acid repeat units include the following:
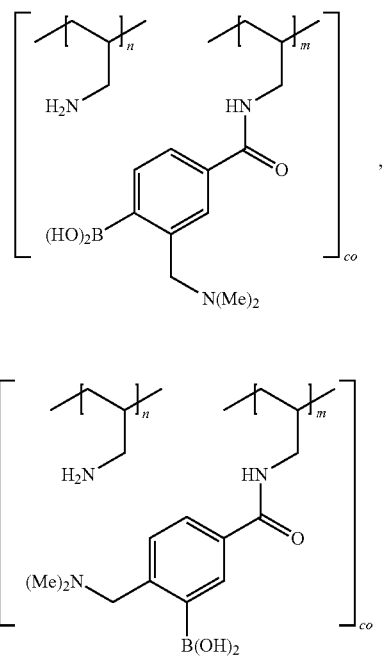

Suitable nitrogen-containing cationic monomeric repeat units include, but not limited to, for example, the following:

where "n" represents an integer from 1 to 100,000.

If desired, the cationic polymers that contain pendant boronic acid groups can also include a hydrophobic group, e.g., a pendent hydrophobic group. As used herein hydrophobic groups are moieties that are more soluble in octanol than water (as a separate chemical entity). For example, an octyl substituent is a hydrophobic group because octane is more soluble in octanol than in water. Suitable hydrophobic groups are C6 or greater linear, branched or cyclic hydrocarbons that can be substituted, for example with one or more hydroxy, halo, and/or aryl (e.g., benzyl) groups.

Additional repeat units that can be included in the polymers described herein, when desired, include neutral and acid repeat units, such as, polyacrylates, polyalkylene glycols, polystyrene, polyvinyl alcohols, polyvinylphosphates, polyvinylsulfates, and the like.

Particular examples of polymers of this disclosure include

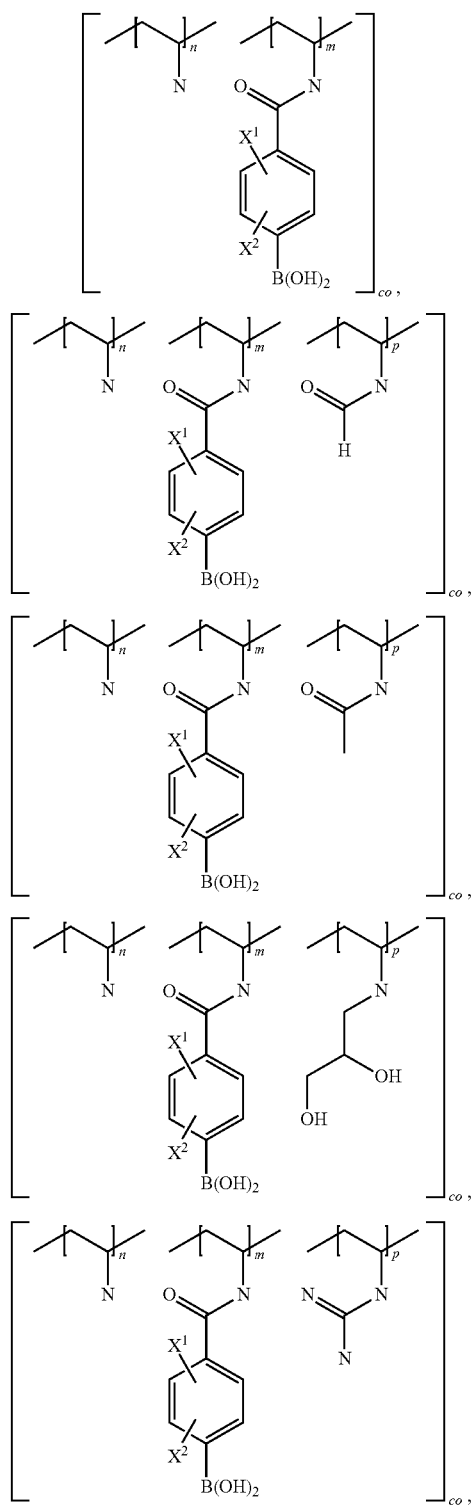

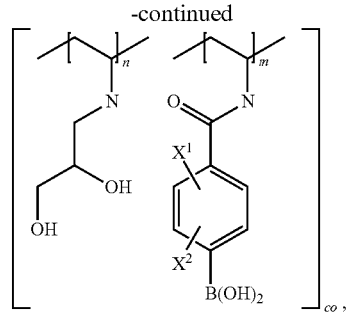

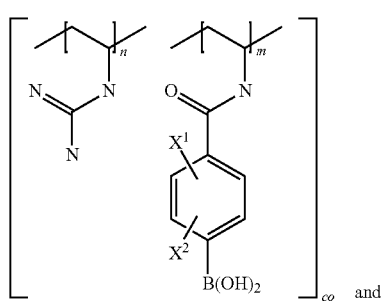

and

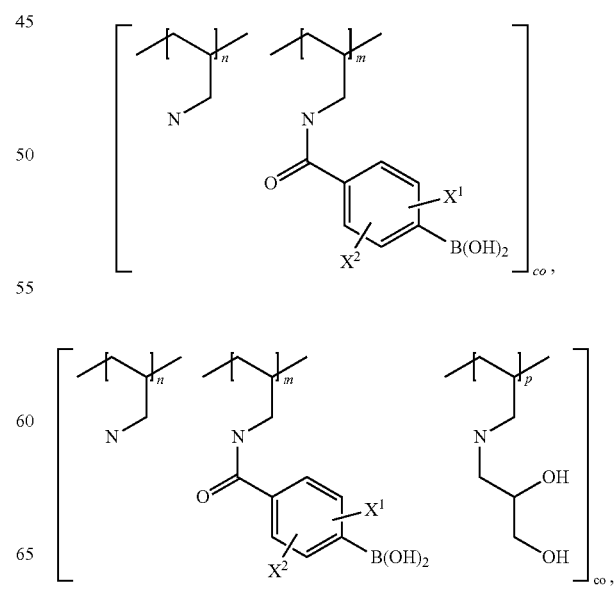

Additional, particular examples of polymers of this disclosure include

-continued
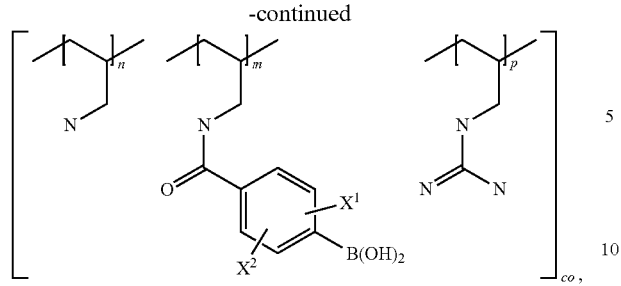
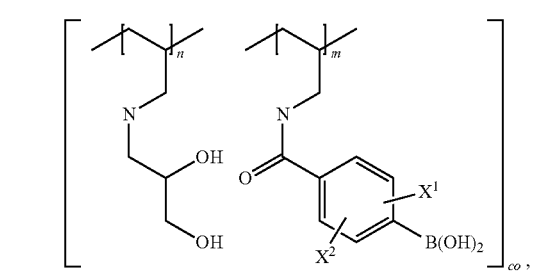
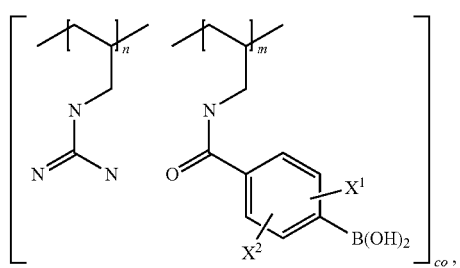
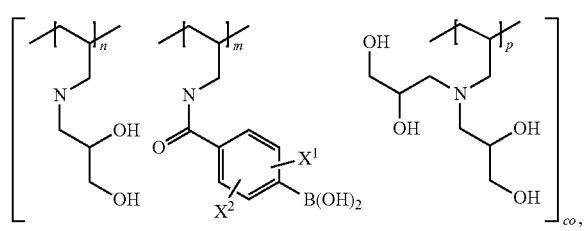
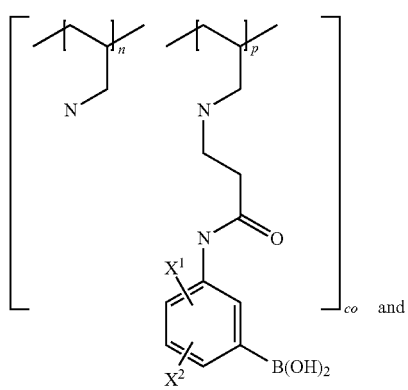
-continued
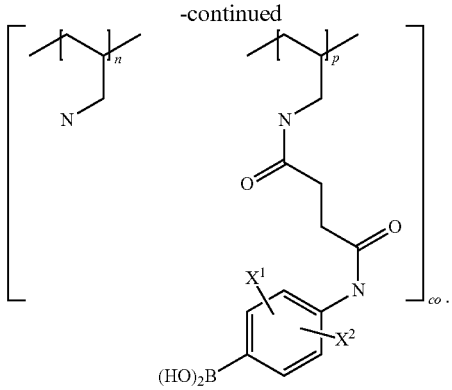
Additional particular examples of polymers of this disclosure include
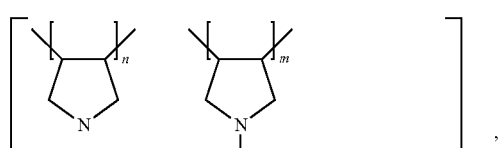
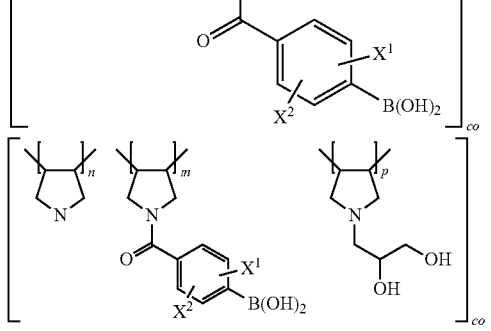
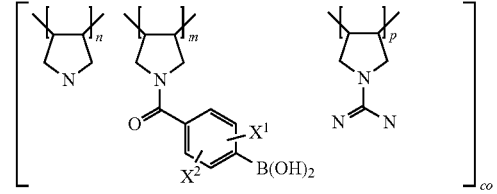
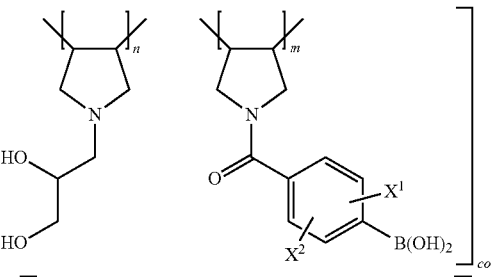
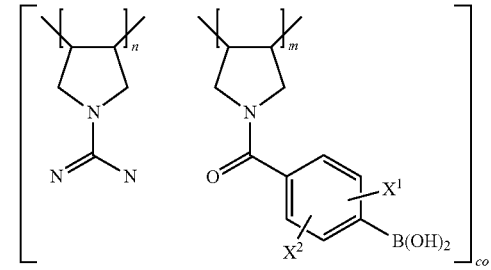
Additional particular examples of polymers of this disclosure include

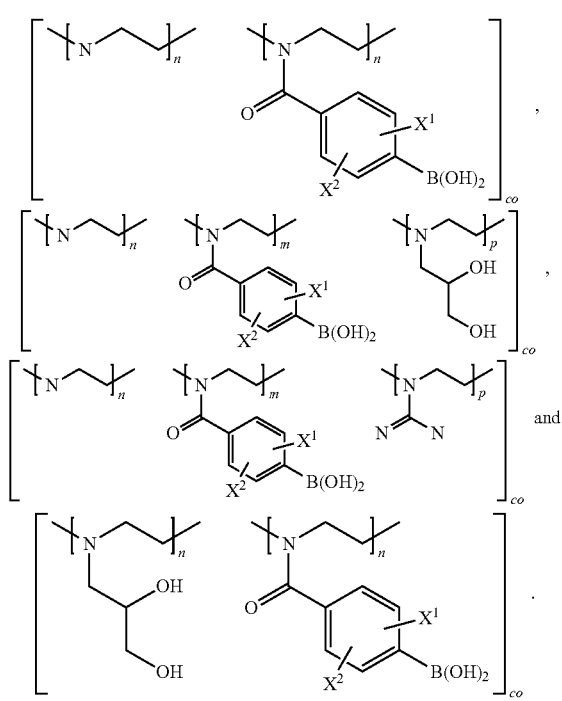

Additional particular examples of polymers of this disclosure include

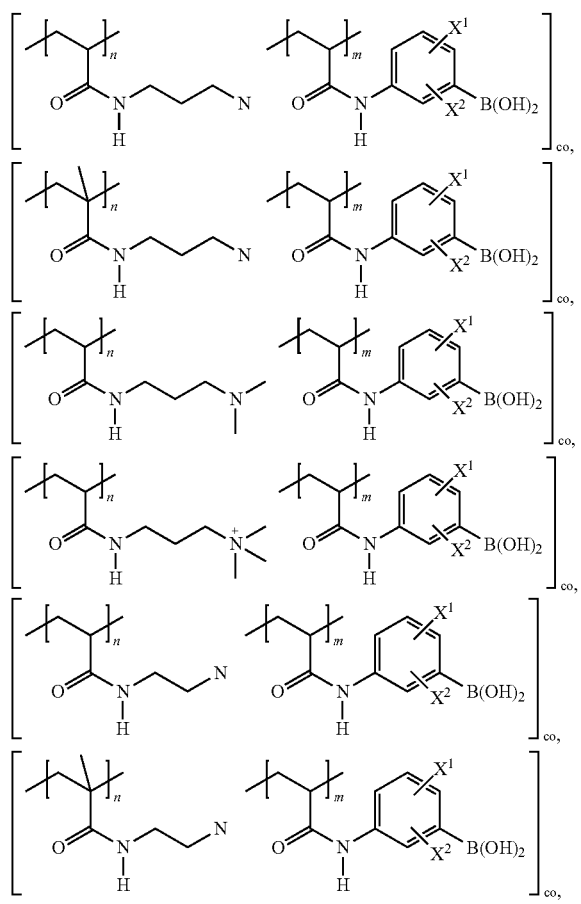

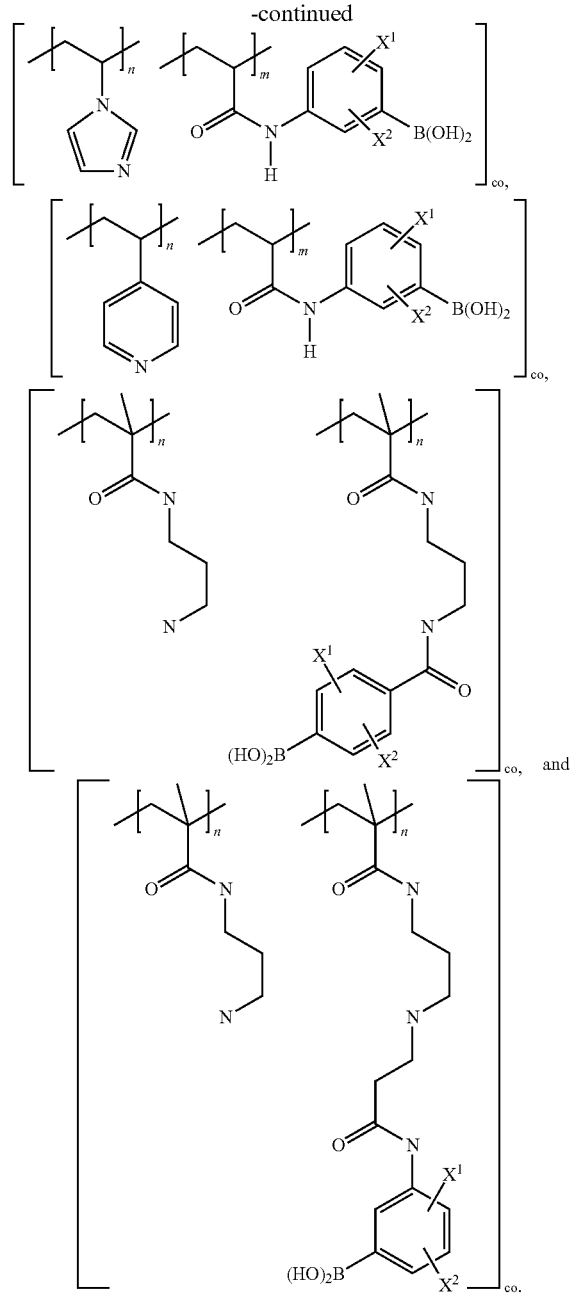

Copolymers of the present invention can exist in a variety of forms. Suitable forms include block copolymers, graft copolymers, comb copolymers, star copolymers, dendrimers, hyperbranched copolymers, random copolymers, gradient block copolymers, and alternate copolymers.

This disclosure also relates to cationic polymers that contain pendant hydrophobic groups, and to the use of such polymers for treating metabolic disease as disclosed herein.

Preferably, the polymers disclosed herein are of sufficient size so that the polymers are substantially not absorbed when administered orally to a subject, such as a human. The threshold molecular weight above which polymers are not absorbed from the GI tract into the systemic circulation is dependent on the specific polymer and conditions in the GI tract and other factors, but it is generally recognized that polymers of greater than 1,000 Da are not substantially absorbed from the GI tract into the systemic circulation. Accordingly, the compositions of this invention that are substantially not absorbed from the GI tract are substantially free of polymer chains smaller than 1,000 Da, and preferably 5,000 Da or more preferably 10,000 Da and have average molecular weights (MW) of at least about 10,000 Da and preferably in the range of 20,000 to 250,000 Da or greater. The polymers of the invention can contain a distribution of polymer chain lengths, and may have a polydispersity index (PDI) in the 1.5-4.0 range, but they contain substantially no material under 1,000 Da, preferably they contain no material under 5,000 Da or more preferably under 10,000 Da.

The inventive polymers are soluble and are preferably not cross-linked. In some embodiments the polymers may be lightly cross-linked but remain soluble and do not form an extended network or gel.

Also included in the present invention are pharmaceutically acceptable salts of the disclosed polymers. For example, polymers which have acid functional groups can also be present in the anionic, or conjugate base, form, in combination with a cation. Suitable cations include alkaline earth metal ions, such as sodium and potassium ions, alkaline earth ions, such as calcium and magnesium ions, and unsubstituted and substituted (primary, secondary, tertiary and quaternary) ammonium ions. Polymers which have basic groups such as amines can also be protonated and have a pharmaceutically acceptable counter anion, such as halides (Cl— and Br—), $CH_3OSO_3^-$, $HSO_4^-$, $SO_4^{2-}$, $HCO_3^-$, $CO_3^{2-}$, nitrate, hydroxide, persulfate, sulfite, acetate, formate, sulfate, phosphate, lactate, succinate, propionate, oxalate, butyrate, ascorbate, citrate, dihydrogen citrate, tartrate, taurocholate, glycocholate, cholate, hydrogen citrate, maleate, benzoate, folate, an amino acid derivative, a nucleotide, a lipid, or a phospholipid. Similarly, ammonium groups comprise a pharmaceutically acceptable counteranion. Boronic acid groups can react with anions such as sodium or potassium hydroxide, alkoxide or carboxylate to form a salt such as —$B$—$(OH)_3Na^+$, —$B$—$(OH)_3K^+$, —$B$—$(OH)_2(OCH_3)Na^+$, —$B$—$(OH)_2(OCH_3)K^+$, —$B$—$(OH)_2(OCOCH_3)Na^+$, —$B$—$(OH)_2(OCOCH_3)K^+$, and the like.

The polymers disclosed herein are typically provided as a mixture of polymer chains with some variability in chain length. This distribution of polymer chain lengths can be measured using size exclusion chromatography (SEC) and a detector capable of measuring polymer molar mass such a multi-angle laser light scattering (MALLS). This method can also confirm the absence of short, low molecular weight polymer chains. It can also provide a polydispersity index (PDI), which is typically considered to be the ratio Mw/Mn, where Mw is the weight fraction-average molecular weight and $M_n$ is the number average molecular weight.

$$PDI = M_w / M_n$$

Values of $M_w$, $M_n$ and PDI can be obtained by SEC, preferable with a MALLS detector. For synthetic polymer materials made from standard free-radical processes, it is common to find PDI values greater than 2, and even greater than 3. In contrast, living free radical polymerization processes such as atom transfer radical polymerization (ATRP) or reversible addition fragmentation chain transfer (RAFT) are capable of producing materials with PDI less than 2, or even less than 1.5.

The polymers disclosed herein can be prepared using any suitable methods, such as by direct polymerization of one, two or more monomers or by polymer modification.

Polymerization can be accomplished using techniques known in the art of polymer synthesis (See, for example, Shalaby et al, ed., Water-Soluble Polymers, American Chemical Society, Washington, D.C. [1991]). Several cationic monomers are available as hydrochloride salts and can be polymerized by methods known in the art, for example, via a free radical addition process. In this case, the polymerization mixture includes a free-radical initiator. Suitable free-radical initiators include azobis(isobutyronitrile), azobis(4-cyanovaleric acid), 2,2'-azobis(2-amidinopropane)dihydrochloride, potassium persulfate, ammonium persulfate, and potassium hydrogen persulfate. Other suitable initiators include ionizing radiation and ultraviolet light. The free radical initiator is preferably present in the reaction mixture in an amount ranging from about 0.01 mole percent to about 5 mole percent relative to the monomer.

Polymer modification approach employs polyamines and copolymer approach employs acrylamide derivatives. "M" in the reaction schemes represents a group that includes a substituted phenyl boronic acid moiety.

Polyamines can serve as mucus-interacting agents as well as starting materials for chemical modification with boronic acid groups. Exemplary polyamines include polyethyleneimine, hydroxyethylated polyethyleneimine, polyamidoamine (PAMAM) dendrimers, poly(allylamine) (PAAn) and its copolymers, poly(diallylamine) (PDAAn) and its copolymers, poly(vinylamine) and its copolymers, poly(vinylimidazole) and its copolymers, poly(vinylpyridine) and its copolymers, poly(vinylaniline) and its copolymers, amine containing acrylamide and methacrylamide copolymers, and the like. Preferred polyamines include poly(allylamine) (PAAn), poly(diallylamine) (PDAAn), poly(ethyleneimine) (PEI) and poly(methacrylamidopropylamine) (PMAPAn).

Polyamine derivatives can be obtained from the chemical modification of polyamines by amide-forming chemistry using EDC coupling (Scheme 1).

Scheme 1: Amide-forming reaction of a polyamine with a carboxylic acid using EDC as a coupling reagent.

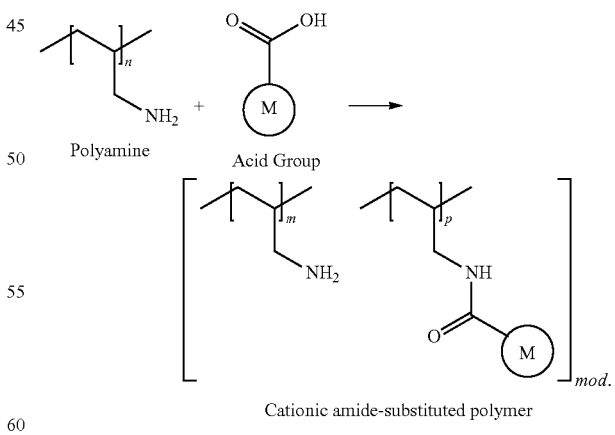

Cationic amide-substituted polymer

A 1% wt/vol of desired polyamine is prepared in deionized water the pH is adjusted to 5.0. Ethanol or other suitable organic is added to the polymer solution at 50% of initial polymer solution volume. The M-carboxylic acid to be coupled is placed into water at 25% of initial polymer solution volume to form a solution or slurry. The EDC coupling agent is dissolved in ethanol or other suitable solvent at 25% of initial polymer solution volume. The EDC solution is then mixed with the M-carboxylic acid solution or slurry. The combined EDC/M-carboxylic acid solution is added to the polymer solution dropwise by pipette or pressure equalizing addition funnel, over approximately 10 minutes. The reaction solutions contains polymer at about 0.5% wt/vol with about 62% vol water and about 38% vol ethanol or other suitable organic solvent. The reaction is stirred and pH is maintained at 5.0. With pH stabilized at 5.0, the reaction is allowed to stir at room temperature for about 18 hours. The polymer is precipitated with excess (3× volume) acetone.

The polyamine derivatives can be obtained from the chemical modification of polyamines by Michael addition reaction. The polyamine is the nucleophile and the acrylamides are the Michael acceptor (Scheme 2).

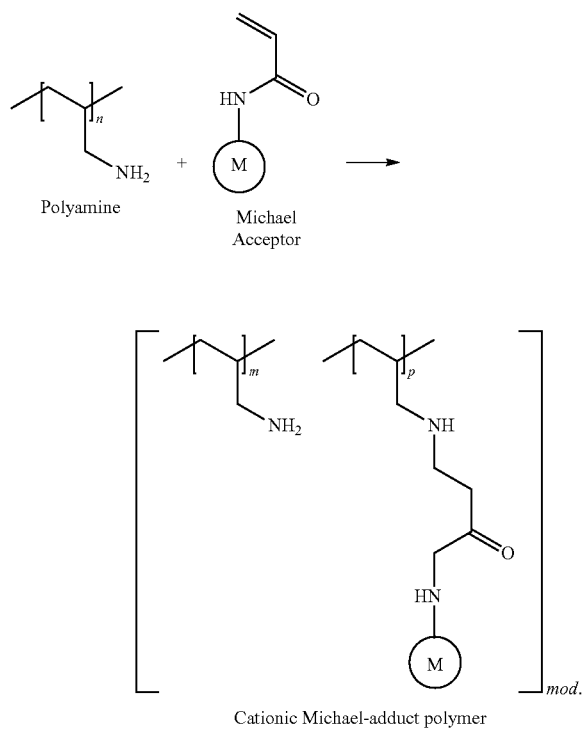

Scheme 2: Michael addition reaction of a polyamine nucleophile with an acrylamides Michael acceptor.

A 1% wt/vol of desired polyamine is prepared in deionized water and the pH was adjusted to 8.5. This pH can be increased or lowered depending on level of modification desired. The desired M-acrylamide is dissolved in ethanol or other suitable solvent at 20% of initial polymer solution volume. The acrylamide solution is then added to the polymer solution to form a reaction mixture with the polymer at about 0.83% wt/vol with about 83% vol water and about 17% vol ethanol or other suitable solvent. The reaction mixture is heated to 70° C. and stirred for 48 hours. The polymer is precipitated with excess (3× volume) acetone.

The polyamine derivatives can be obtained from the chemical modification of polyamines by hydroxyalkylation using epoxide-opening chemistry (Scheme 3).

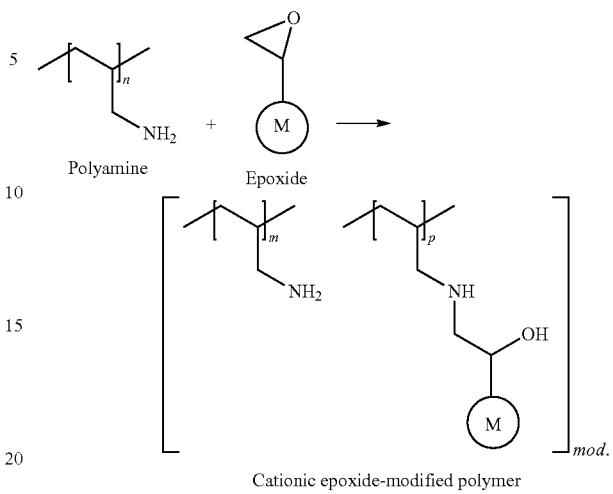

Scheme 3: Reaction of a polyamine with an epoxide.

A 2% wt/vol of desired polyamine is prepared in deionized water and the pH is adjusted to 6.0. This pH can be increased or lowered depending on level of modification desired. The desired M-epoxide is dissolved in water/ethanol (25%/75%) at 100% of initial polymer solution volume. This solution is then added to the polymer solution to prepare a reaction solution in which the polymer was about 1% wt/vol with about 62% vol water and about 38% vol ethanol. The reaction mixture was heated at 60° C. for 48 hr. If the epoxide is not fully in solution at 60° C., a small portion of additional ethanol may be added to aid in solubility. The polymer is precipitated with excess (3× volume) acetone.

Polyacrylamide derivatives can be obtained, for example, by the polymerization of 3-acrylamidopropylamine with a desired M-acrylate or M-acrylamide (Scheme 4).

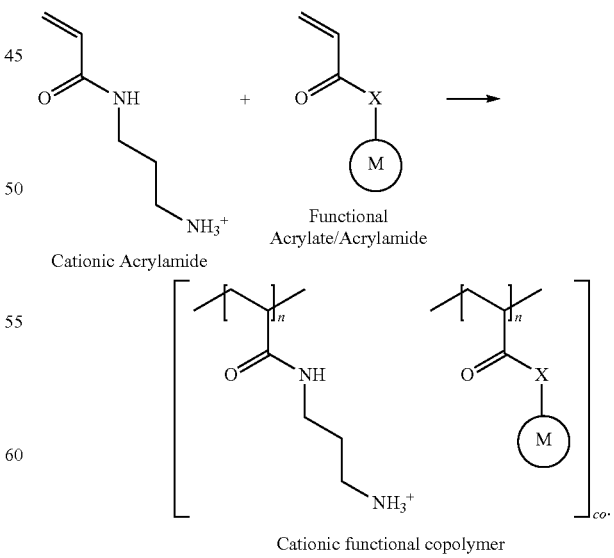

Scheme 4: Reaction of an acrylamide with an acrylate.

A desired amount of the desired M-acrylate or M-acrylamide monomer is placed into a 30 ml glass vial equipped with magnetic stirring and an N2 (g) inlet. The desired M-acrylate or M-acrylamide monomer is dissolved in dimethylformamide or other suitable water-miscible organic solvent. The desired amount of cationic, neutral or anionic co-monomer is then added. A small amount of water will likely be needed to fully dissolve the charged co-monomer in a binary solvent system. An appropriate amount of AIBN initiator is added. The co-monomer solution is N2 (g) purged for at least ~15 minutes. The reaction is then heated at 65° C. while under a blanket of $N_2$ (g). After several hours of heating, the copolymer solution or suspension is isolated by precipitation from acetone. The addition of some water and adjustment to lower pH will be needed for some of the polymers to facilitate precipitation in acetone. Finally, the product may be dissolved in deionized water, IPA/dry ice frozen and lyophilized.

Accordingly, in some aspects, the invention provides a method for applying a physical barrier to the gastrointestinal (GI) tract of a subject between the intestinal lining and the luminal contents. The method includes administering to the GI tract of the subject a therapeutic effective amount of a polymer described herein.

As used herein, the term "physical barrier" or "luminal barrier" refers to a complex of polymer and mucus that prevents or reduces chyme from contacting the mucosal epithelium located under the polymer-mucus complex in the intestinal tract. The physical barrier is created when the polymer combines in-situ with the anionic mucins contained within the mucus lining the wall of the intestines. The physical barrier can be substantially complete or partial. A substantially complete physical barrier extends to substantially cover an entire target area, such as the epithelial lining of the proximal duodenum. A partial physical barrier extends to cover a portion of a target area, such as a portion of the epithelial lining of the duodenum. For example, a partial barrier can cover at least about 1%, 5%, 10%, 20%, 25%, 30%, 40%, 50% or more of the epithelium at the target site.

The partial physical barrier can be discontinuous and spatially distributed, and may have varying degrees of permeability. For instance, physical barrier can be a semipermeable complex of polymer and mucus or mucins on the luminal surface of the intestines, preferably in the duodenum.

In embodiments, the physical barrier or a formulation thereof is passed by natural digestive processes of the subject. In yet other embodiments, the physical barrier is removable or reversible by the ingestion of a liquid or solvent.

The polymers described herein bind tightly to the mucus and mucins to form a polymer-mucus complex that is resistant to disassociation (e.g., by high salt and low pH). Accordingly, once formed, the physical barrier will typically be present for a "retention period" or "residence time," and is removed by the natural actions of the digestive system. Typical retention periods can range from about half an hour to about 7 days, including time period ranging from about 1 hour to about 3 hours, about 1 hour to about 5 hours, about 1 hour to about 24 hours, about 1 to about 3 days, and others.

The desired residence time can vary depending on the clinical application and can be adjusted based on the amount of polymer that is administered, and the frequency and interval between administrations. For instance, up to 50% of subjects with T2DM have gastroparesis, or delayed gastric emptying, that may require the mucoadhesive lining to remain in place for a longer time than a pre-diabetic or non-diabetic obese subject. Blood glucose levels spike often within the first two hours of eating a meal, most often within the first 60 minutes; thus, the lining should adhere for a minimum of 60 minutes in one embodiment. In another embodiment, in the case of pre-diabetic subjects who may not take medication prior to every meal, and thus may not comply with a treatment that would require to change their behavior, a longer lasting mucoadhesive lining may be required. In this application, the lining may adhere for a minimum of 6-8 hours with a maximum of 24 hours could be required. Residence time will also be influenced by the mucus layer at which the polymer develops the most affinity to. For instance, the superficial, loosely adherent layer sloughs off on the order of minutes to hours, whereas affinity to the deeper firmly adherent layer would lead to a longer lasting mucoadhesive coating. Overall, residence time can be tuned to various clinical and technical considerations in the embodiments outlined in this disclosure.

Polymers of the invention can form an occlusive barrier layer in the proximal intestine, specifically the duodenum. Preferably, the occlusive barrier is formed in the proximal duodenum or duodenal bulb. The polymers are therefore fully capable of forming a barrier layer immediately upon release from the stomach and entry into the proximal duodenum.

The polymers are administered orally in any suitable dosage form. A variety of dosage forms that are suitable for oral administration are well-known in the art and include, liquid formulations (e.g., solutions, suspensions, slurrys, syrups), gels, ointments, powder, tablets, caplets, capsules and the like.

In one example, the polymers can be administered in a liquid form and are typically sufficiently stable and soluble in the stomach allowing immediate delivery to the duodenum in an active state without requiring further swelling, solubilization, or equilibration with the surrounding milieu. The polymers described herein are typically polyamines, which undergo some degree of deprotonation as they transition from the highly acidic stomach (pH~2) to the duodenum (pH ~5) which targets the complexing activity of the polymers to the duodenum. However, the polymers may also form a barrier layer in the stomach.

In other examples, the polymer is administered in a solid form capable of being hydrated in the stomach. The solid form can be formulated to provide slow dissolution, which can protect the polymers from gastric acidity, but resulting in the polymers entering the proximal duodenum in a fully active state. In other examples, the polymers are administered in the form of an enteric-coated tablet, caplet, capsule or other enteric-coated dosage form to protect the polymers from gastric acidity. In such examples, the enteric coating is formulated to dissolve or degrade as soon as possible after or during passage through the pyloric valve (when the pH increases from pH~2) permitting the immediate release of the polymers. Such dosage forms can include a superdisintegrant to facilitate immediate release of the polymers at the desired site in the intestinal tract, such as the proximal duodenum. Suitable superdisintegrant excipients are well-known in the art. (See, e.g., Mohanachandran, P. S. et al, Superdisintegrants: An Overview, *Int. J. Pharma. Sci. Review and Research*, (2011) 6:1 pp 105-109.) For example, enteric capsules have been described in the literature that are capable of targeting delivery to the duodenum. (See, e.g., Reix N. et al. Intl J Pharm (2012) 422:1-2 pp. 338-340.)

The polymers of the invention can quickly dissolve after oral administration in the stomach, in the duodenum or on other mucosal surfaces.

In some aspects, the pharmaceutical formulations of the polymers of this invention may optionally include a calcium salt, such as calcium chloride or calcium citrate. It is believed that the physical barrier formation can be accelerated in the presence of a calcium salt.

If desired, the polymers can be administered to the gastrointestinal tract of the subject via an endoscope, a nasal feeding tube, an oral feeding tube, or similar device. The polymer can also be sprayed onto the mucosa at the desired site of action, for example, the spraying can be done endoscopically.

For therapeutic purposes, a "therapeutically effective amount" of the polymer is administered. A therapeutically effective amount, as used herein is an amount sufficient to affect the desired response under the conditions of administration, including clinical response. The therapeutically effective amount may be sufficient, for example, to improve glucose homeostasis, to reduce insulin resistance, to cause weight loss, and/or to improve other signs and/or symptoms of T1DM, T2DM or other metabolic disorders such as hyperlipidemia, non-alcoholic steatohepatitis, non-alcoholic fatty liver and other conditions such as obesity and overweight. For example, a therapeutically effective amount can be an amount sufficient to lower blood glucose levels and/or reduce HbA1C.

The precise amount that is administered will depend on a number of well-known considerations, including the age, weight, gender, particular condition to be treated and its severity, sensitivity to drugs, and overall health of the subject. A skilled clinician can determine appropriate amounts to administer based on these and other considerations. Typically, 1 to 5 tablets/capsules are administered per dose, each of size 0 or 0E or 00 or 00E or 000. A dose can be administered one, two, three or four times per day. The dose timing will be based on the underlying indication. Preferably, a dose is administered at least 5, 10, 15, 30 or 60 min and not more than 12 hrs before a meal for the treatment of metabolic conditions. For other indications, dosing right before or along with food may be preferred.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

This disclosure relates to methods of treating metabolic disease by administering a therapeutically effective amount of a polymer disclosed herein to a subject in need thereof. Metabolic diseases that can be treated using the method include, for example, glucose intolerance, T1DM, T2DM, prediabetes, hyperlipidemia, obesity, overweight, obesity, dyslipidemia, hypertension, hyperglycemia, impaired glucose tolerance, insulin resistance, metabolic syndrome, non-alcoholic steatohepatitis (NASH), non-alcoholic fatty liver disease (NAFLD) and polycystic ovary syndrome (PCOS).

This disclosure also relates to methods of treating gastrointestinal disorders by administering a therapeutically effective amount of a polymer disclosed herein to a subject in need thereof. Gastrointestinal disorders that can be treated using the method include, for example, celiac disease, irritable bowel syndrome, inflammatory bowel disease, colitis, *Clostridium difficile*, endotoxemia, diarrhea and constipation.

The methods of the invention are also useful in addressing leaky gut syndrome and associated conditions. Leaky gut syndrome is a term of art that describes a condition in which there is increased intestinal permeability due to alteration/damage to the tight epithelial junctions which results in a compromised epithelial barrier function. This impaired barrier acts as a conduit for intraluminal macromolecules and antigens to permeate through the gut wall triggering inflammatory, immunological reactions that result in various health conditions. For example, leaky gut syndrome has been implicated in IBS (irritable bowel syndrome). Certain proteins in foods can behave as antigens eliciting an immune response. For example, in Celiac disease, preventing gluten from coming into contact with the epithelium can reduce the immunological response. Leaky gut has also been implicated in other immunological conditions like Inflammatory Bowel Disease (Crohn's disease, Ulcerative Colitis). An enhanced intestinal barrier can reduce the absorption of endotoxins in the gastrointestinal tract. Some of these endotoxins are a result of normal bacterial metabolism/breakdown or due to bacterial overgrowth. This is particularly relevant in patients with impaired liver function, e.g., in liver cirrhosis, in whom the endotoxins are not metabolized (detoxified) by the liver resulting in impaired brain function (called hepatic encephalopathy). Thus the methods described herein can be used to enhance the barrier properties of the intestine and can treat or reduce the incidence of hepatic encephalopathy. Uremia is another condition associated with an impairment of intestinal barrier function that can be treated or reduced using the methods described herein. Similarly, the methods described herein can be used to treat or reduce the incidence of Chronic Kidney Disease (CKD), as clinical evidence has documented greater intestinal permeability in patients with advanced CKD.

The therapeutic methods can also provide benefit by reducing the clinical biomarkers associated with a variety of disorders, such as reducing systemic inflammation, oxidative stress and hyperuricemia.

The disclosed polymers can be administered to the subjects in the form of a pharmaceutical composition that includes a pharmaceutically acceptable carrier, excipient, buffer or diluent.

For oral administration, the pharmaceutical compositions of the invention may be presented in dosage forms such as capsules, tablets, caplets, powders, granules, gels, suspensions, solutions or other suitable dosage form. Capsule may be gelatin, soft-gel or solid. Tablet, caplet and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants.

Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation. Suitable pharmaceutical formulations for oral administration and methods for preparing them are well-known in the art. See, e.g., Remington: The Science and Practice of Pharmacy, twentieth edition, 2000.

Pharmaceutical preparations that can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. Methods for encapsulating compositions (such as in a coating of hard gelatin or cyclodextran) are known in the art (Baker, et al., "Controlled Release of Biological Active Agents", John Wiley and Sons, 1986).

The methods of the invention include a co-formulation of the polymeric composition comprising with probiotics. Probiotic formulations assist in building the beneficial probiotic bacteria in the intestinal tract. It is known in the art that probiotics have significant effects on the reduction of blood sugar, HbA1c, insulin levels and insulin resistance in subjects with diabetes. Suitable probiotics include, but not limited to *Lactobacillus Bifidobacteria, Saccharomyces boulardii*, and *Bacillus coagulans, Akkermansia muciniphila, Bifidobacterium* spp, *Escherichia* spp. Methods to prepare formulations containing probiotics are well known in the art.

If desired, the therapeutic methods described herein can include co-administration of the polymeric compositions with one or more additional therapeutic agents. Therapeutic agents for co-administration in subjects with diabetes may include classes of drugs that are GLP-1 receptor agonists, DPP-4 inhibitors, SGLT-2 inhibitors, glucosidase inhibitors, insulin, metformin, sulfonylureas and thiazolidenediones.

In particular examples, the additional therapeutic agent is one or more agent indicated for the treatment of diabetes (type 1 and/or type 2), pre-diabetes, hyperglycemia, impaired glucose tolerance or insulin resistance. Such agents include biguanides (e.g., metformin), sulfonylureas (e.g., limepiride, gliclazide, gilpizide, glimepiride, tolbutamide, glibenclamide (glyburide), gliquidone, and glyclopyramide), meglinithinides (e.g., repaglinide and nateglinide); thiazolidindiones (e.g., pioglitazone and rosiglitazone), alpha-glucosidase inhibitors (e.g., acarbose and miglitol), dipeptidyl peptidase 4 (DPP4) inhibitors (e.g., vildagliptin, sitagliptin, saxagliptin, and linagliptin), GLP-1 analogues (e.g., exenatide, lixisenatide, dulaglutide, and liraglutide), sodium-glucose co-transporter 2 (SGLT2) inhibitors (e.g., dapagliflozin, ganagliflozin, and empagliflozin), amylin mimetics (e.g., pramlinitide), D2-dopamine agonists (e.g., bromocriptine), bile acid sequestrants (e.g., cholestyramine, colesevelam, colestilan, and colestimide), and insulin (e.g., human insulin, insulin glulisine, insulin lispro, insulin isophane human, insulin zinc suspension mixed bovine, insulin protamine zinc bovine, insulin isophane porcine, insulin isophane human, and the like).

The co-therapeutic methods can provide several advantages over monotherapy. For example, administering the polymer and an additional therapeutic agent can enhance the efficacy of and/or reduce the amount of additional therapeutic agent that is needed for the desired effect. Accordingly, undesired side effects of the additional therapeutic agent can be reduced or eliminated. Additionally, the polymers of the invention and the additional therapeutic can provide superior therapy in comparison to each agent as a monotherapy, and co-therapy can provide additive or synergistic effects.

The subject to be treated by the presently disclosed methods is typically a mammal and preferably a human subject. Suitable subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Preferably, the subject is a human including, but not limited to, fetal, neonatal, infant, juvenile, and adult humans.

The terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

The term "about," when referring to a value means±20%, or ±10. Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

As used herein, the term "alkyl" refers to monovalent aliphatic hydrocarbon typically containing 1 to about 6 carbon atoms. An alkyl group can be straight chain, branched chain, monocyclic moiety or polycyclic moiety or combinations thereof. Suitable substituents for an alkyl group include aryl, —OH, halogen (—Br, —Cl, —I and —F), —O(R'), —O—CO—(R'), —CN, —NO$_2$, —COOH, —NH$_2$, —NH(R'), —N(R')$_2$, —COO(R'), —CONH$_2$, —CONH(R'), —CON(R')$_2$, —S(O)R', —S(O)$_2$R', —SH and —S(R'). Each R' is independently an alkyl group or an aryl group. A substituted alkyl group can have more than one substituent. Examples of alkyl groups include methyl, ethyl, propyl, isopropyl, butyl, iso-butyl, sec-butyl, tert-butyl, pentyl, hexyl, cyclopropyl, cyclobutyl, cyclopentyl, cyclohexyl, norbornyl, and the like.

As used herein, the term "alkylene" refers to —(CH$_2$)$_x$—, that may be optionally substituted, where x is an integer between 1 to 5. Preferably, x is between 1 to 3, more preferably x is 1 or 2. Suitable substituents for an alkylene group are identical to those for alkyl groups.

As used herein, the term "alkoxy" refers to a group of formula —O— alkyl. Example of alkoxy groups include methoxy, ethoxy, propoxy (e.g., n-propoxy and isopropoxy), tert-butoxy, and the like.

As used herein, the term "aryl," refer to stable aromatic monocyclic ring system having 3-7 ring atoms, of which all the ring atoms are carbon, and which may be substituted or unsubstituted. Aryl substituents include, —OH, halogen (—Br, —Cl, —I and —F), —O(R'), —O—CO—(R'), —CN, —NO$_2$, —COOH, —NH$_2$, —NH(R'), —N(R')$_2$, —COO(R'), —CONH$_2$, —CONH(R'), —CON(R')$_2$, —S(O)R', —S(O)$_2$R', —SH and —S(R'). Each R' is independently an alkyl group.

As used herein, the term "aryloxy" refers to a group of formula —O— aryl. The aryl group may optionally substituted.

As used herein, the term "electron withdrawing" refers to an atom or a group that draws electron density from neighboring atoms towards itself, usually by resonance or inductive effects. Suitable electron withdrawing groups include, but not limited to halo, —CN, —NO$_2$, —N$^+$(R$^9$)(R$^{10}$)(R$^{11}$), —CF$_3$, —SO$_3$(R$^9$), —SO$_2$(R$^9$), and —CON(R$^9$)(R$^{10}$).

As used herein, the term "electron donating" refers to an atom or a group that donates electron density to neighboring atoms, usually by resonance or inductive effects. Suitable electron donating groups include, but not limited to alkyl, amino, —(CH$_2$)$_m$—N(R$^9$) (R$^{10}$), and —OR$^9$.

As used herein, the term "hydroxy" refers to a group of formula —OH.

As used herein, "halo" or "halogen" refers to F, Cl, Br, or I.

As used herein, the phrase "optionally substituted" means unsubstituted or substituted. As used herein, the term "substituted" means that a hydrogen atom is removed and replaced by a substituent. It is to be understood that substitution at a given atom is limited by valency.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

I. Synthesis

Reagents: Poly(allylamine hydrochloride) was obtained from Nittobo Medical, Japan (PAAn-HCl, Cat #PAA-HCl-3L, 50.3% solution in water) and used as received. The material was qualified by 1H-NMR, TGA, and size exclusion chromatography (SEC-MALLS). 1-(3-Dimethylaminopropyl)-3-ethylcarbodiimide hydrochloride was obtained from Chem-Impex International, Wood Dale, Ill. (EDC-HCl, Cat #00050, 99.8%) and used as received. The material was qualified by 1H-NMR, FT-IR, and melting point. 1-Hydroxybenzotriazole hydrate was obtained from Chem-Impex International, Wood Dale, Ill. (HOBt, Cat #24755, 99.8% (odb), 21.3% water) and used as received. The material was qualified by 1H-NMR, and FT-IR. 4-Carboxyphenylboronic acid was obtained from Chem-Impex International, Wood Dale, Ill. (CPBA, Cat #28086, 99.7%) and used as received. The material was qualified by 1H-NMR, FT-IR, and melting point. 3-Trifluoromethyl-4-Carboxyphenylboronic acid was obtained from Combi-Blocks Inc., San Diego, Calif. (CF3-CPBA, Cat #FA-2133, 98%) and used as received. The material was qualified by 1H-NMR, and FT-IR. 3-Fluoro-4-Carboxyphenylboronic acid was obtained from AOB Chem, Zhuhai, China (F-CPBA, Cat #10055, 97%) and used as received. The material was qualified by 1H-NMR, FT-IR, and melting point. 2,3-Difluoro-4-Carboxyphenylboronic acid was obtained from Combi-Blocks Inc., San Diego, Calif. (Di-F-CPBA, Cat #FA-3733, 96%) and used as received. The material was qualified by 1H-NMR, and FT-IR. 3-Dimethylaminomethyl-4-Carboxyphenylboronic acid pinacol ester was obtained from Combi-Blocks Inc., San Diego, Calif. (Me2N-CPBA, Cat #PN-4078, 96%) and used as received. The material was qualified by 1H-NMR, and FT-IR EXAMPLE 1. SYNTHESIS OF PAAn modified with 4-Carboxyphenylboronic acid: PAAn-HCl 50.3% solution (5.964 g, 32 mmol of amine equivalents) was placed in a 250 ml beaker with a magnetic stir bar and deionized water (90 ml). The resulting clear solution was magnetically stirred, and a pH electrode introduced. The pH was adjusted to 8.0 by dropwise addition of a 1N NaOH solution while stirring. 4-Carboxyphenylboronic acid, 99.7% (0.907 g, 5 mmol) was added to the reaction mixture and the resulting suspension was stirred. After 20 minutes of stirring, the pH had dropped to 6.8 and some solid remained suspended in solution. Additional NaOH solution was added in portions with stirring to cause the complete dissolution of the suspension. The pH of the resulting clear solution was 7.5. Solid HOBt-hydrate powder (0.046 g, 0.25 mmol) was then added to the clear reaction solution and dissolved after 20 minutes of stirring. Hydrochloric acid (1N) was added to the reaction mixture to lower the pH to 5.4. The reaction solution remained clear. EDC-HCl (1.152 g, 6 mmol) dissolved in 10 ml of deionized water was then slowly pipetted into the reaction mixture. The clear reaction mixture had a final volume of 120 ml and a pH of 5.6. This reaction mixture was stirred for 18-hours. The reaction mixture was pH adjusted to 2.5 with TN HCl and then subjected to dialysis against a 2.5% NaCl solution using tangential flow filtration on a Pall Minimate™ TFF system. After removal of 5-diafiltration volumes and desalting until the filtrate had a conductivity of <200 ρS/cm, the retentate solution was collected in a lyophilization jar. The solution was frozen in an IPA/dry-ice slurry and lyophilized until dry (3-days). A yield of 1.492 g was obtained as a fluffy white solid. The 1H-NMR spectrum (D20/DCl) confirmed the expected structure.

EXAMPLE 2: SYNTHESIS OF PAAn modified with 3-Trifluoromethyl-4-Carboxyphenylboronic acid: PAAn-HCl 50.3% solution (0.5088 g, 2.74 mmol of amine equivalents) was placed in a 30 ml glass vial with a magnetic stir bar and deionized water (9.0 ml). The resulting clear solution was magnetically stirred, and a pH electrode introduced. The pH was adjusted to 8.0 by dropwise addition of a TN NaOH solution while stirring. 3-Trifluoromethyl-4-Carboxyphenylboronic acid, 98% (0.1148 g, 0.491 mmol) was added to the reaction mixture and the resulting suspension was stirred. After 20 minutes of stirring, the pH had dropped to 6.8 and some solid remained suspended in solution. Additional NaOH solution was added in portions with stirring to cause the complete dissolution of the suspension. The pH of the resulting clear solution was 7.5. Solid HOBt-hydrate powder (0.0088 g, 0.0514 mmol) was then added to the clear reaction solution and dissolved after 20 minutes of stirring. Hydrochloric acid (1N) was added to the reaction mixture to lower the pH to 5.4. The reaction solution remained clear. EDC-HCl (0.1143 g, 0.596 mmol) dissolved in 1.0 ml of deionized water was then slowly pipetted into the reaction mixture. The clear reaction mixture had a final volume of 10 ml and a pH of 5.6. This reaction mixture was stirred for 18-hours. The reaction mixture was precipitated into excess acetone. The precipitated solid was dissolved in water, the pH adjusted to 2.8 with 1N HCl and then subjected to dialysis purification using 6K to 8 k MWCO cellulose membrane dialysis tubing (Spectrum Laboratories) for 8-hours against acidified water (pH=2-3), and then three additional water changes over 2-days. The solution contained within the dialysis bag was collected in a lyophilization jar. The solution was frozen in an IPA/dry-ice slurry and lyophilized until dry (3-days). A yield of 263 mg was obtained as a fluffy white solid. The 1H-NMR spectrum (D20/DCl) confirmed the expected structure.

EXAMPLE 3: SYNTHESIS OF PAAn modified with 3-Fluoro-4-Carboxyphenylboronic acid: PAAn-HCl 50.3% solution (5.964 g, 32 mmol of amine equivalents) was placed in a 250 ml beaker with a magnetic stir bar and deionized water (90 ml). The resulting clear solution was magnetically stirred, and a pH electrode introduced. The pH was adjusted to 8.0 by dropwise addition of a 1N NaOH solution while stirring. 3-Fluoro-4-carboxyphenylboronic acid, 97% (1.034 g, 5 mmol) was added to the reaction mixture and the resulting suspension was stirred. After 20 minutes of stirring, the pH had dropped to 6.8 and some solid remained suspended in solution. Additional NaOH solution was added in portions with stirring to cause the complete dissolution of the suspension. The pH of the resulting clear solution was 7.5. Solid HOBt-hydrate powder (0.046 g, 0.25 mmol) was then added to the clear reaction solution and dissolved after 20 minutes of stirring. Hydrochloric acid (1N) was added to the reaction mixture to lower the pH to 5.4. The reaction solution remained clear. EDC-HCl (1.152 g, 6 mmol) dissolved in 10 ml of deionized water was then slowly pipetted into the reaction mixture. The clear reaction mixture had a final volume of 120 ml and a pH of 5.6. This reaction mixture was stirred for 18-hours. The reaction mixture was pH adjusted to 2.5 with 1N HCl and then subjected to dialysis against a 2.5% NaCl solution using tangential flow filtration on a Pall Minimate™ TFF system. After removal of 5-diafiltration volumes and desalting until the filtrate had a conductivity of <200 µS/cm, the retentate solution was collected in a lyophilization jar. The solution was frozen in an IPA/dry-ice slurry and lyophilized until dry (3-days). A yield of 1.492 g was obtained as a fluffy white solid. The 1H-NMR spectrum (D20/DCl) confirmed the expected structure.

EXAMPLE 4: SYNTHESIS OF PAAn modified with 2,3-Difluoro-4-Carboxyphenylboronic acid: PAAn-HCl 50.3% solution (0.5027 g, 2.70 mmol of amine equivalents) was placed in a 30 ml glass vial with a magnetic stir bar and deionized water (9.0 ml). The resulting clear solution was magnetically stirred, and a pH electrode introduced. The pH was adjusted to 8.0 by dropwise addition of a 1N NaOH solution while stirring. 2,3-Difluoro-4-Carboxyphenylboronic acid (0.1029 g, 0.510 mmol) was added to the reaction mixture and the resulting suspension was stirred. After 20 minutes of stirring, the pH had dropped to 5.6 and some solid remained suspended in solution. Additional NaOH solution was added in portions with stirring to cause the complete dissolution of the suspension. The pH of the resulting clear solution was 7.5. Solid HOBt powder (0.0082 g, 0.0479 mmol) was then added to the clear reaction solution and dissolved after 20 minutes of stirring. Hydrochloric acid (1N) was added to the reaction mixture to lower the pH to 5.5. The reaction solution remained clear. EDC-HCl (0.1018 g, 0.531 mmol) dissolved in 1.0 ml of deionized water was then slowly pipetted into the reaction mixture. The clear reaction mixture had a final volume of 10 ml and a pH of 5.5. This reaction mixture was stirred for 18-hours. The reaction mixture was precipitated into excess acetone. The precipitated solid was dissolved in water, the pH was adjusted to 2.8 with 1N HCl and the solution was subjected to dialysis purification using 6K to 8 k MWCO cellulose membrane dialysis tubing (Spectrum Laboratories) for 8-hours against acidified water (pH=2-3), and then three additional water changes over 2-days. The contents of the dialysis bag were collected in a lyophilization jar. The solution was frozen in an IPA/dry-ice slurry and lyophilized until dry (3-days). A yield of 235 mg was obtained as a fluffy white solid. The 1H-NMR spectrum (D20/DCl) confirmed the expected structure.

EXAMPLE 5: SYNTHESIS OF PAAn modified with 3-Dimethylaminomethyl-4-Carboxyphenylboronic Acid: PAAn-HCl 50.3% solution (0.4973 g, 2.67 mmol of amine equivalents) was placed in a 30 ml glass vial with a magnetic stir bar and deionized water (9 ml). The resulting clear solution was magnetically stirred, and a pH electrode introduced. The pH was adjusted to 8.0 by dropwise addition of a 1N NaOH solution while stirring. Solid 3-Dimethylaminomethyl-4-Carboxyphenylboronic acid pinacol ester (0.1565 g, 0.458 mmol) was added to the reaction mixture and the resulting suspension was stirred. After 20 minutes of stirring, the pH had dropped to 5.1 and some solid remained suspended in solution. Additional NaOH solution was added in portions with stirring to cause the complete dissolution of the suspension. The pH of the resulting clear solution was 8.0. Solid HOBt powder (0.0088 g, 0.0514 mmol) was then added to the clear reaction solution and dissolved after 20 minutes of stirring. Hydrochloric acid (1N) was added to the reaction mixture to lower the pH to 5.5. The reaction solution remained clear. EDC-HCl (0.1048 g, 0.547 mmol) dissolved in 1.0 ml of deionized water was then slowly pipetted into the reaction mixture. The clear reaction mixture had a final volume of 10 ml and a pH of 5.5. This reaction mixture was stirred for 18-hours. The reaction mixture was precipitated into excess acetone, 2×. The collected precipitate was dissolved in de-ionised water and the solution was frozen in an IPA/dry-ice slurry and lyophilized until dry (3-days). A yield of 271 mg was obtained as a fluffy white solid. The 1H-NMR spectrum (D20/DCl) confirmed the expected structure, and also showed that the pinacol ester group had been hydrolyzed from the boronic acid.

II. Mucin-Mixing Observational Assay

The scheme for the mucin mixing assay is shown in FIG. 1.

When a water-soluble mucin glycoprotein is mixed with a soluble polymeric complexing agent, a variety of outcomes may result. The solution may remain clear or become cloudy or even opaque. The physical state of the mixture may remain homogeneous and flowable, or it may contain particles or even take on a gel-like appearance. The degree of opacity and the physical appearance of the mixture provides a qualitative assessment of the interaction between the complexing agent and mucin, and more importantly, the physical properties of the complex that is formed.

The inventors seek polymers capable of forming extended network structures when mixed with mucin. They have found that when certain polymers are combined with mucin glycoprotein in solution, complexation may be observed by the appearance of gel-like or opaque mixtures with substantial phase separation. Conversely, in the absence of complexation, the solution may remain clear and flowable. In seeking polymers capable of strong mucin complexation, they are interested in classifying such mixtures according to well-defined descriptors of clarity and physical state.

For example, in some cases, a dispersion may be formed. In a dispersion, no particulate is visible. Dispersions may be stable for days without settling or aggregation. In other cases, a suspension of small particles may be formed. A suspension may settle out over time (hours, days), but is generally stable and can be re-suspended by mixing. There is literature precedent for use of a turbidity metric derived from optical absorbance at a particular visible light wavelength, and relationship of this metric to assess the degree of complexation in some related experiments involving complex formation involving polymers.

However, in some cases, mucin complexation by certain polymers results in gross precipitation of larger particles, sometimes with irregular or complex morphology. This may be an indication of extended network formation. In some instances, these precipitated solids have adhesive properties, adhering to the walls of the vial in which the mixing experiment is performed. In some cases, complex fiber-like precipitates or gels are formed. Furthermore, many cases of gross precipitation are accompanied by phase separation (syneresis) where the polymer/mucin complex is deposited as an adherent film or a gel-like mass, and a separate liquid phase (usually clear or only slightly hazy) is observed. In cases of gross precipitation such as these, it is likely that the degree of complexation is very high, and it is informative to classify the morphology and appearance of the mucin/polymer complex in comparison to related materials.

The objective of this assay is to determine whether the polymers of the invention are capable of forming an insoluble complex when mixed with a soluble mucin glycoprotein under a set of standard conditions, and to observe the general properties of the resulting mixture.

The assay outputs are assignment of a clarity descriptor, assignment of a physical state descriptor and optional descriptions and comments.

Isolation of a water-soluble fraction of Sigma (cat #1778) mucin from porcine stomach, Type-3 (MPS-3): The protocol is as follows. 1.0 g of MPS-3 is mixed with 40 ml of MilliQ deionized water in a 50 mL conical tube. The suspension was left overnight by attaching the tubes to a rotating carousel mixer. The 50 ml conical tube was then centrifuged on a Beckman Avanti centrifuge (5,300 rpm for 60 minutes). The supernatant was poured carefully into a fresh 50 ml conical tube trying to not disturb the solid pellet at the bottom. Centrifugation was then repeated on the supernatant (Beckman Avanti centrifuge, 5,300 rpm for 60 minutes). The supernatant was again collected into a tared 50 ml conical tube. The mucin solution was frozen at −80° C. for at least 2 hrs. The frozen sample was placed on a lyophilizer for at least 3-days. The lyophilized product was collected, the tube weighed, and % yield calculated, with an expected recovery of 0.60-0.65 g. The solid was stored at 2-5° C. in the refrigerator.

Preparation of 0.1 M MES-Saline Buffer: 21.3 g of (2-(N-morpholino)ethanesulfonic acid monohydrate) (MES, J. T. Baker Bioreagent, >98%) was added into a 1-liter bottle. 9.0 g of Sodium Chloride (Fisher Chemical, USP grade) was added into the bottle. A 1-liter graduated cylinder was filled with mQ deionized water (DIW, 18 MΩ). Approximately 750 ml of DIW was added to the bottle, capped and shaken to dissolve all solids. A magnetic stirring bar and a pH electrode were added to the bottle, and stirring initiated. 1N of NaOH solution was added in portions to bring the solution pH to 6.0 (or other desired pH), noting the volume of solution added. The required amount of additional DIW was added to provide a total volume of 1-liter. The bottle was capped and the buffer was stored at 2-5° C.

Polymer/mucin mixing turbidity and observational assay: A 1.0% w/w solution was made of each test polymer using MES-Saline buffer, pH adjusted to 6.0. A 1.0% w/w solution of water-soluble MPS-3 was made using MES-Saline buffer, pH adjusted to 6.0. The mucin solution was slightly hazy. 0.25-0.5 mL of the MPS-3 solution was placed into a 2-dram (4 mL) vial. An equivalent volume of the test polymer solution was slowly added to the vial. The vial capped and slowly rotated to mix while observing any physical changes. One of the following descriptors for the clarity of the mixtures can be selected to read the resulting mixture: clear (only slight hazy, similar to initial mucin solution); hazy (more hazy than initial mucin solution, can read text through it); cloudy (non-transparent, can't read through it, but transmits light well); opaque (like milk, no transparency, does not transmit much light) and not applicable (material shows gross phase separation). One of the following descriptors on the physical state of the mixtures can be selected to read the resulting mixture: clear; dispersion (no visible particles); suspension (very fine particulate is observable), precipitate (large irregular particles, may be adherent) and phase separation (films, gels are deposited, a clear or hazy supernatant fluid may be seen). The mixtures in capped vials were observed for approx. 1 hour to note any changes.

Results of mucin-mixing observational assay: Following the protocol above, a set of test compounds were tested for their ability to form insoluble complexes with mucin in MES buffer at pH=5.5, 6.0, and 6.5. Polymer solutions were made at least 1-hour before the experiment and allowed to mix gently on a rotisserie. Total dissolution was confirmed for all test polymer before beginning the experiment.

TABLE 1

| Polymer | Mucin-Mixing Result (clarity/physical-state) | | |
|---|---|---|---|
| | pH = 5.5 | pH = 6.0 | pH = 6.5 |
| PAAn-HCl | 2/B | 2/B | 2/B |
| Example-1 | 2/B | 2/B | 5/E |
| Example-2 | 2/B | 5/E | 5E |
| Example-3 | 5/E | 5/E | 5/E |
| Example-4 | 5/E | 5/E | 5/E |

The results of the mucin-mixing assay show that when the parent polymer, PAAn-HCl, is mixed with mucin, a hazy dispersion is obtained at all pH values. This result suggests that in this case, the polymer/mucin complex does not form an extended network structure. When the modified PAAn of Example-1 is mixed with mucin, a similar hazy dispersion is observed at pH=5.5 and 6.0. However, at pH=6.5 strong phase separation is observed with a white film depositing on the vessel walls. At this higher pH value, the polymer of Example-1 is capable of acting as a mucin crosslinking agent, forming an extended network structure.

The polymers of Example-2, 3, and 4, are derivatives of the Example-1 polymer. They contain an additional electron withdrawing substituent group on the phenylboronic acid ring. For these polymers, particularly Example-3 and 4, the strong phase separation behavior is observed at all pH values examined in this experiment. This additional substitution activates the phenylboronic acid resulting in a stronger interaction with mucin. This stronger interaction causes the observed stronger and more robust extended network formation at pH=6.0 and in some cases at pH=5.5.

III. Surface Plasmon Resonance (SPR) Study on Mucin-Interacting Polymers

This example describes an investigation of the interaction of soluble polymers with a mucin-coated surface. Surface Plasmon Resonance (SPR) was used to quantify the binding of mucin-interacting polymers in solution flowing over a mucin-coated SPR chip. The binding of these polymers was compared to assess how the degree of substitution affects polymer on binding to the mucin surface.

The SPR experiment was executed using the Bio-Rad XPR36 ProteOn™ SPR instrument and ProteOn™ LCP sensor chip. Specifically, we observed a set of identical water-soluble poly(allylamine) polymers differing only in the extent of substitution with the mucophilic group, 3-fluoro-CPBA. Robustness of the surface-deposited material was then challenged by exposure to 1M NaCl. The output of the study is a sensorgram produced by the Bio-Rad ProteOn™ XPR36 instrument and associated software. The sensorgram output directly indicates quantitative surface attachment of polymer to the modified surface. A fresh, newly purchased LCP sensor chip was used for this experiment.

Preparation of biotinylated Mucin: Biotinylation of MPS-3 water soluble fraction: A water soluble fraction MPS-3 was prepared as described under the mucin-mixing observational assay. Soluble fraction MPS-3 (42 mg) was dissolved in 30 ml of PBS buffer at pH 7.2 and filtered through a 0.45 m PES syringe filter, then a 0.2 m syringe filter to obtain a clear colorless solution. (+)-biotin N-hydroxysuccinimide ester (Sigma, #H1759) (25 mg) was dissolved in DMF (2 mL) to obtain a clear solution. The entire 2 mL DMF solution of (+)-biotin N-hydroxysuccinimide ester was added dropwise via pipette to 18 ml of the MPS-2 PBS solution. The mixture was rocked on a shaker at room temperature for 4-hours covered in aluminum foil. The reaction mixture was placed in a dialysis tubing (SpectraPor MWCO=6-8 kDa) and the dialysis bag was placed into a 5-gallon pail of deionized water with slow stirring. The dialysis was allowed to continue for at least 48 hours. The retentate (pH found to be 6.55) was collected in a lyophilization jar and the material was frozen in a dry-ice/acetone bath and lyophilized. The product was collected as a white fluffy solid (12 mg) and stored in a freezer (−20° C.).

SPR Operations: Coating the ProteOn chip with biotinylated mucin: The ProteOn LCP chip was inserted in to the ProteOn XPR36 instrument. PBS Buffer (pH=6.0) was flown through all 6-lanes of the chip at 100 ul/min for 3-5 minutes. A solution of biotinylated mucin (5 ug/ml) in PBS (pH=6.0) was flown through all 6-lanes of the chip at 25 ul/min for 600 seconds. The sensorgram response was accessed to assure that saturation coverage is achieved as indicated by stable RU readings. PBS Buffer (pH=6.0) was flown through all 6-lanes of the chip at 100 ul/min for 3-5 minutes. The SPR sensorgram response was accessed towards stability of the bound mucin layer.

Test polymer-mucin interaction and resistance to wash-off: Six different test polymer solutions (4 ug/ml) were flown through the 6-lanes of the mucin modified LCP chip at 100 ul/min for 240 seconds. The sensorgram response was assessed to assure that saturation coverage is achieved as indicated by stable RU readings. PBS Buffer (pH=6.0) was flown through all 6-lanes of the chip at 100 ul/min for 3-5 minutes. The SPR sensorgram response was assessed. 1 M NaCl PBS Buffer (pH=6.0) was flown through all 6-lanes of the chip at 100 ul/min for 18 seconds. PBS Buffer (pH=6.0) was flown through all 6-lanes of the chip at 100 ul/min for 3-5 minutes. The SPR sensorgram response to NaCl treatment was assessed.

Results of SPR study: A stable mucin layer was formed by flowing 5 ug/ml biotinylated MPS-3 over the Bio-Rad LCP chip: After establishing a steady baseline in flowing buffer solution, exposure of the SPR chip to a solution of 5 ug/ml biotinylated MPS-3 resulted in a steady accumulation of material on the LCP chip. The rapid increase in signal intensity rolled-over after 50 seconds and stabilized indicating that the surface was saturated with a stable mucin layer.

Binding of PAAn-Fluoro-CPBA polymers to the mucin-coated SPR chip was affected by the degree of substitution. After establishing a reproducible and stable mucin layer on a new SPR chip, four different polymer solutions were simultaneously flowed through the lanes of the microfluidic chip. The polymer solutions were allowed to flow over the chip for an extended period so that the RU signal had time to roll-over and establish equilibrium for each polymer. All PAAn-fluoro-CPBA derivatives strongly bound to the mucin surface. Surface binding was found to be dependent on the level of fluoro-CPBA substitution of the polymer. PAAn-fluoro-CPBA(15) gave the strongest surface binding (1470 RU) followed by PAAn-fluoro-CPBA(10) (1286 RU), and PAAn-fluoro-CPBA(6) (1149 RU). Unsubstituted PAAn also showed strong binding to the mucin surface, but to a lesser degree (1002 RU).

Exposure of the polymer-bound mucin surface to a strong salt solution (1M NaCl) strongly reduced the adsorbed PAAn surface, but the PAAn-(Fluoro-CPBA) surfaces were stable. After flowing the polymer solutions over the surface long enough to reach a near equilibrium RU signal, buffer solution again was flowed over the surface demonstrating the stability of the surface coatings as a stable RU signal in each lane. Then, a strong salt solution (1M NaCl) was passed over the mucin chip in a short burst (18 seconds) followed by a return to flowing buffer solution.

The short exposure to NaCl caused the removal of a significant amount of the adsorbed PAAn (−26%). In contrast, the RU values for the PAAn-fluoro-CPBA materials showed smaller effects (−2%, −5%, −9%), appearing to be more robust to the strong salt treatment with increasing fluoro-CPBA substitution (see Table 2).

TABLE 2

| lane | Polymer | Conc. (ug/ml) | Max RU increase* | Change in RU after 1M NaCl^ |
|---|---|---|---|---|
| 1 | Buffer, PBS pH = 6.0 | — | 0 | +2 |
| 2 | PAAn (NittoBo) | 4 | 1002 | −264 (−26%) |
| 3 | PAAn-fluoro-CPBA (6) | 4 | 1149 | −109 (−9%) |
| 4 | PAAn-fluoro-CPBA (10) | 4 | 1286 | −60 (−5%) |
| 5 | PAAn-fluoro-CPBA (15) | 4 | 1470 | −35 (−2%) |

A set of three PAAn-fluoro-CPBA polymers with variable levels of Fluoro-CPBA substitution were evaluated for binding to a mucin modified surface by SPR. The greatest surface binding was seen for PAAn-Fluoro-CPBA(15), with the lower substituted polymers binding to a lesser extent. Unsubstituted PAAn also bound the mucin surface, but to a smaller degree.

The SPR surface coated with PAAn-Fluoro-CPBA polymers were stable to treatment with concentrated salt solution. This contrasts the behavior of unsubstituted PAAn which lost a substantial percentage of bound polymer when treated with salt. This is likely due to the exclusively coulombic association of PAAn with the mucin surface, which is effectively screened in the presence of a high concentration of salt. For the PAAn-Fluoro-CPBA materials, the combined Coulombic and mucophilic interactions of these modified polymers make their mucin complex stable to strong salt conditions.

IV. Single Dose Efficacy Study

Animal Model: The Goto-Kakazaki (GK) rat model was selected based on the extensive literature evidence for response of the GK rat model to surgical- and device-induced duodenal exclusion. The GK rat model is one of the most well validated rodent models for Type 2 diabetes drug evaluation. The GK rat is a polygenic non-obese Wistar substrain that develops adult onset Type 2 diabetes early in life. GK rats are an ideal Type 2 diabetes model, exhibiting characteristics such as retinopathy, nephropathy, neuropathy, and cardiovascular complications similar to those seen in human disease. Most significantly, this substrain has been extensively studied in bariatric surgical models, demonstrating an improvement in glucose tolerance subsequent to bariatric surgery similar to that of humans. Oral glucose tolerance testing (OGTT) was used to evaluate the single dose efficacy of the polymer therapy in the GK rat model.

Figure 2:
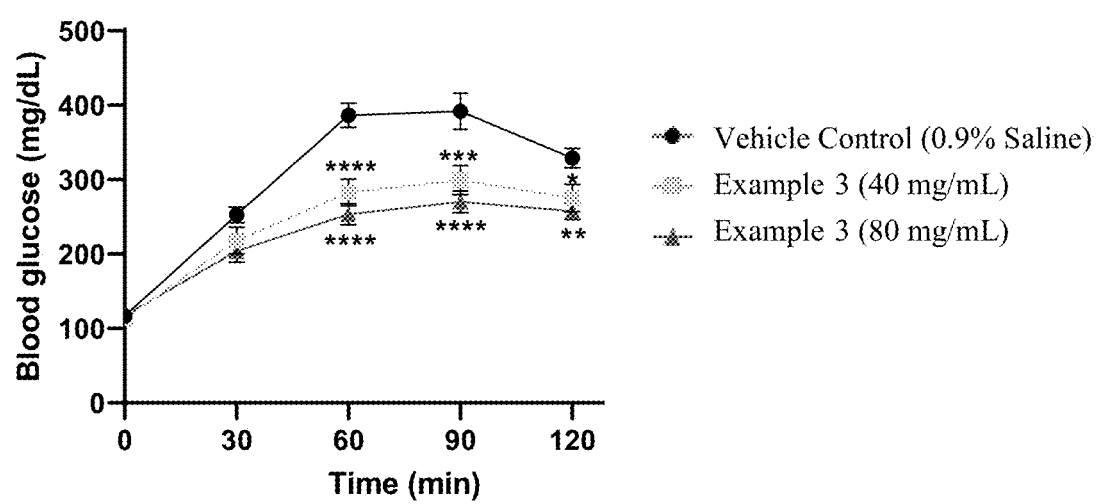
FIG. 2 illustrates the results of an oral glucose tolerance test on vehicle control (0.9% Saline) and treatment groups treated with 40 mg/mL of Example-3 and 80 mg/mL of Example-3 respectively.

General Procedure: Prior to experimentation, all rats were fasted for 15-hours with access to water. Animals were split into three test groups with n=6-7 rats each: (Group A) Vehicle Control which received 0.9% saline; (Group B) Treatment at 40 mg/mL concentration of Example-3 dissolved in 0.9% saline; and (Group C) Treatment at 80 mg/mL concentration of Example-3 dissolved in 0.9% saline. All rats received a standard 1.5 mL volume of their respective solutions delivered by oral gavage in an identical fashion. After 60 minutes, baseline blood glucose levels were measured. Oral gavage of 40% glucose solution (2.0 g/kg rat) was given immediately after recording the baseline blood glucose measurement. Glucose tolerance test samples were then taken from each rat at 30-, 60-, 90-, and 120-minutes following glucose administration (see FIG. 2). The time dependent blood glucose values were analyzed and plotted using GraphPad Prism 8 software. Two-way ANOVA was applied to raw data to evaluate multiple comparisons between all groups and time points. Incremental Area under the Curve was calculated using zero as baseline for the Y parameter; percentage reduction was calculated manually, and t-tests applied to verify significance between treated groups versus the vehicle control.

Figure 3:
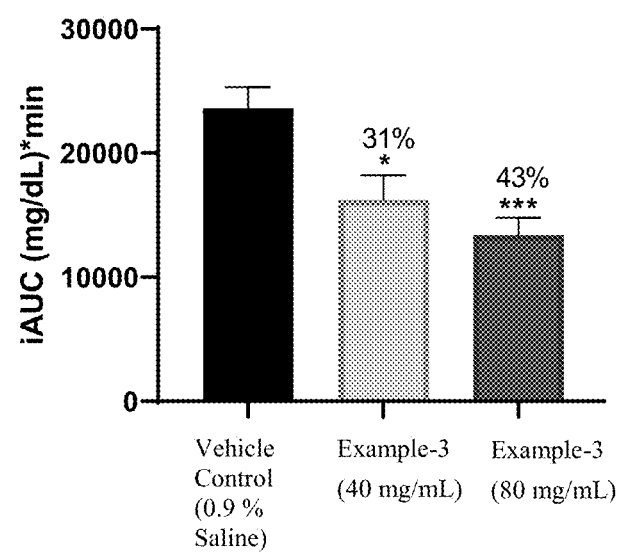
FIG. 3 compares the reduction in the incremental area under the blood glucose curve (iAUC) for the vehicle control (0.9% Saline) and treatment groups treated with 40 mg/mL of Example-3 and 80 mg/mL of Example-3 respectively.

Results: The Treatment groups at 40 mg/mL and 80 mg/mL showed a statistically significant and dose dependent reduction in incremental Area Under Curve (iAUC) of 31% and 43%, respectively, when compared to the Vehicle Control (see FIG. 3), thereby demonstrating the efficacy of the polymers of the disclosure. Significance was demonstrated at time 60, 90, and 120 minutes in each Treatment group with p-values noted in FIG. 2 and FIG. 3 as: * $p<0.05$,  $p<0.01$, * $p<0.001$, **** $p<0.0001$.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A pharmaceutical composition comprising a polymer that comprises the structure:

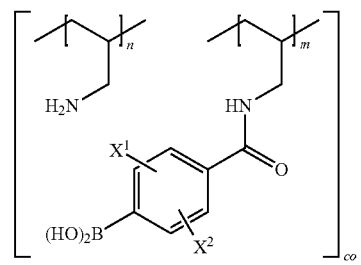

or a pharmaceutically acceptable salt thereof, wherein:

$X^1$ and $X^2$ are each independently selected from a group consisting of hydrogen, halo, and —$CF_3$, with the proviso that no more than one of $X^1$ and $X^2$ is hydrogen; and each n and m are independently an integer from 1 to 100,000, wherein co denotes copolymer; and optionally one or more of an excipient, adjuvant, binder, diluent, disintegrant, filler, or lubricant; and wherein the pharmaceutical composition is for oral administration.

2. The pharmaceutical composition of claim 1, wherein at least one of $X^1$ and $X^2$ is halo.

3. The pharmaceutical composition of claim 2, wherein the halo is fluoro.

4. The pharmaceutical composition of claim 1, wherein the composition is in a dosage form selected from the group consisting of a powder, a tablet, a caplet, a granule, and a capsule.

5. The pharmaceutical composition of claim 4, wherein the dosage form is a capsule.

6. The pharmaceutical composition of claim 1, wherein the polymer has mucin complexing activity.

7. The pharmaceutical composition of claim 1, wherein the polymer is water soluble.

8. The pharmaceutical composition of claim 1, wherein about 5% to about 50% of units in the polymer have the structure

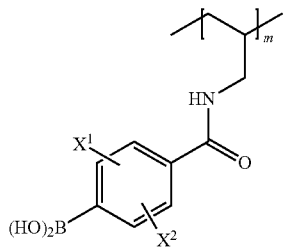

9. The pharmaceutical composition of claim 1, wherein about 5% to about 20% of units in the polymer have the structure

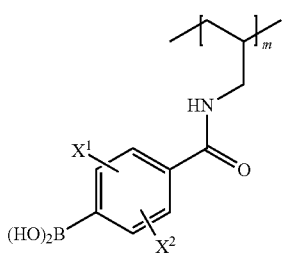

10. The pharmaceutical composition of claim 1, wherein $X^1$ is hydrogen and $X^1$ is halo.

11. The pharmaceutical composition of claim 1, wherein $X^1$ is hydrogen and $X^1$ is fluoro.

12. The pharmaceutical composition of claim 1, wherein $X^1$ is hydrogen and $X^1$ is —$CF_3$.

13. The pharmaceutical composition of claim 1, wherein $X^1$ and $X^2$ are each halo.

14. The pharmaceutical composition of claim 1, wherein $X^1$ and $X^2$ are each fluoro.

15. The pharmaceutical composition of claim 1, wherein the composition comprises an excipient, adjuvant, binder, diluent, disintegrant, filler, or lubricant disintegrant.

16. The pharmaceutical composition of claim 1, wherein the composition comprises a disintegrant.

17. The pharmaceutical composition of claim 1, further comprising an additional therapeutic agent.

18. The pharmaceutical composition of claim 17, wherein the additional therapeutic agent comprises a GLP-1 receptor agonist, a DPP-4 inhibitor, an SGLT-2 inhibitor, a glucosidase inhibitor, an insulin, a biguanide, a sulfonylurea, a meglitinide, a thiazolidinedione, an amylin mimetic, a D2-dopamine agonist, or a bile acid sequestrant.

19. The pharmaceutical composition of claim 1, wherein the polymer can form a physical barrier between an intestinal lining and luminal contents when administered to the gastrointestinal tract of a subject.

\* \* \* \* \*